US011385241B2

(12) United States Patent
Eden et al.

(10) Patent No.: US 11,385,241 B2
(45) Date of Patent: Jul. 12, 2022

(54) METHODS OF PROGNOSIS AND TREATMENT

(71) Applicant: MeMed Diagnostics Ltd., Tirat HaCarmel (IL)

(72) Inventors: Eran Eden, Haifa (IL); Kfir Oved, Hof HaCarmel (IL); Assaf Cohen-Dotan, Natania (IL); Roy Navon, Tel-Aviv (IL); Olga Boico, Haifa (IL); Meital Paz, Haifa (IL)

(73) Assignee: MeMed Diagnostics Ltd., Tirat HaCarmel (IL)

( * ) Notice: Subject to any disclaimer, the term of this patent is extended or adjusted under 35 U.S.C. 154(b) by 69 days.

(21) Appl. No.: 16/334,033

(22) PCT Filed: Sep. 27, 2017

(86) PCT No.: PCT/IL2017/051088
§ 371 (c)(1),
(2) Date: Mar. 18, 2019

(87) PCT Pub. No.: WO2018/060998
PCT Pub. Date: Apr. 5, 2018

(65) Prior Publication Data
US 2019/0271709 A1 Sep. 5, 2019

Related U.S. Application Data

(60) Provisional application No. 62/401,296, filed on Sep. 29, 2016.

(51) Int. Cl.
*G01N 33/50* (2006.01)
*G01N 33/52* (2006.01)
*G01N 33/53* (2006.01)
*G01N 33/60* (2006.01)
*G01N 33/68* (2006.01)
*G16H 50/30* (2018.01)
*G16H 50/70* (2018.01)
*G16H 50/20* (2018.01)
*G01N 33/58* (2006.01)
*C07K 14/47* (2006.01)
*C07K 14/525* (2006.01)
*C07K 14/54* (2006.01)
*C07K 14/52* (2006.01)

(52) U.S. Cl.
CPC ......... *G01N 33/6893* (2013.01); *G01N 33/50* (2013.01); *G01N 33/52* (2013.01); *G01N 33/53* (2013.01); *G01N 33/582* (2013.01); *G01N 33/60* (2013.01); *G01N 33/6863* (2013.01); *G01N 33/6869* (2013.01); *G16H 50/20* (2018.01); *G16H 50/30* (2018.01); *G16H 50/70* (2018.01); *C07K 14/4716* (2013.01); *C07K 14/4737* (2013.01); *C07K 14/522* (2013.01); *C07K 14/525* (2013.01); *C07K 14/5412* (2013.01); *G01N 2333/52* (2013.01); *G01N 2333/525* (2013.01); *G01N 2333/5412* (2013.01); *G01N 2800/26* (2013.01)

(58) Field of Classification Search
CPC ............ A61K 39/3955; A61K 38/191; G01N 2800/50; G01N 2800/52; G01N 2800/26; G01N 33/6863; G01N 33/50; G01N 33/52; C07K 14/525; C07K 16/241
See application file for complete search history.

(56) References Cited

U.S. PATENT DOCUMENTS

| | | | |
|---|---|---|---|
| 5,639,617 A | 6/1997 | Bohuon | |
| 5,910,421 A | 6/1999 | Small, Jr. et al. | |
| 6,077,665 A | 6/2000 | Welrich et al. | |
| 6,136,526 A | 10/2000 | Venge | |
| 6,210,661 B1 | 4/2001 | Enssle et al. | |
| 6,709,855 B1 | 3/2004 | Stanton et al. | |
| 6,756,483 B1 | 6/2004 | Bergmann et al. | |
| 6,953,435 B2 | 10/2005 | Kondo et al. | |
| 7,115,717 B2 | 10/2006 | Mori et al. | |
| 7,132,246 B2 | 11/2006 | Bergmann et al. | |
| 7,153,662 B2 | 12/2006 | Bergmann et al. | |
| 7,157,081 B2 | 1/2007 | Bergmann et al. | |
| 7,598,031 B2 | 10/2009 | Lew | |
| 7,629,116 B2 | 12/2009 | Ott | |
| 7,892,539 B2 | 2/2011 | Winoto et al. | |
| 8,021,836 B2 | 9/2011 | Kolopp-Sarda et al. | |
| 8,465,951 B2 | 6/2013 | Rao et al. | |
| 8,507,210 B2 | 8/2013 | Bergmann et al. | |
| 8,563,476 B2 | 10/2013 | Lillard, Jr. | |

(Continued)

FOREIGN PATENT DOCUMENTS

| | | |
|---|---|---|
| CN | 1656378 | 8/2005 |
| CN | 101208602 | 6/2008 |

(Continued)

OTHER PUBLICATIONS

Bone et al. Definitions for sepsis and organ failure and guidelines for the use of innovative therapies in sepsis. Chest 101(6): 1644-1655, 1992.*
Kang et al. Low serum TNF-related apoptosis-inducing ligand (TRAIL) levels are associated with acute ischemic stroke severity. Atherosclerosis 240: 228-233, 2015.*
Michowitz et al. The involvement of tumor necrosis factor-related apoptosis-inducing ligand (TRAIL) in atherosclerosis. J Am Coll Cardiol 45(7): 1018-1024, 2005.*

(Continued)

*Primary Examiner* — Bridget E Bunner

(57) ABSTRACT

A method of determining a management course for treating a subject showing symptoms of a disease is disclosed. The method comprises measuring the TRAIL protein level in a blood sample of the subject, wherein when the TRAIL level is below a predetermined amount, the subject is treated as a high-risk patient.

11 Claims, 14 Drawing Sheets

Specification includes a Sequence Listing.

(56) References Cited

U.S. PATENT DOCUMENTS

| | | | |
|---|---|---|---|
| 8,697,370 | B2 | 4/2014 | Kas et al. |
| 8,821,876 | B2 | 9/2014 | Ginsburg et al. |
| 9,034,328 | B2 | 5/2015 | Takahashi |
| 9,709,565 | B2 | 7/2017 | Eden et al. |
| 9,726,668 | B2 | 8/2017 | Oved et al. |
| 9,850,539 | B2 | 12/2017 | Tsalik et al. |
| 10,209,260 | B2 | 2/2019 | Oved et al. |
| 10,303,846 | B2 | 5/2019 | Eden et al. |
| 10,502,739 | B2 | 12/2019 | Oved et al. |
| 10,859,574 | B2 | 12/2020 | Oved et al. |
| 2004/0038201 | A1 | 2/2004 | Nau et al. |
| 2004/0043379 | A1 | 3/2004 | Hashimoto et al. |
| 2004/0171013 | A1 | 9/2004 | Lilius et al. |
| 2005/0227223 | A1 | 10/2005 | Miyawaki |
| 2005/0233395 | A1 | 10/2005 | Weiser et al. |
| 2006/0052278 | A1 | 3/2006 | Powell |
| 2006/0099628 | A1 | 5/2006 | Ching et al. |
| 2006/0246495 | A1 | 11/2006 | Garrett et al. |
| 2007/0015172 | A1 | 1/2007 | Zhang et al. |
| 2007/0184460 | A1 | 8/2007 | Ching et al. |
| 2007/0231816 | A1 | 10/2007 | Chaussabel et al. |
| 2007/0281319 | A1 | 12/2007 | Kolopp-Sarda et al. |
| 2008/0020379 | A1 | 1/2008 | Agan et al. |
| 2008/0064113 | A1 | 3/2008 | Goix et al. |
| 2008/0171323 | A1 | 7/2008 | Banchereau et al. |
| 2009/0155180 | A1 | 6/2009 | Jump et al. |
| 2009/0203534 | A1 | 8/2009 | Hossain et al. |
| 2010/0028874 | A1 | 2/2010 | Ramachandran et al. |
| 2010/0068147 | A1 | 3/2010 | Hibberd et al. |
| 2010/0143372 | A1 | 6/2010 | Yao et al. |
| 2010/0297611 | A1 | 11/2010 | Sambursky et al. |
| 2011/0059858 | A1 | 3/2011 | Kas et al. |
| 2011/0117563 | A1 | 5/2011 | Filipowicz et al. |
| 2011/0166166 | A1 | 7/2011 | Henkin |
| 2011/0183856 | A1 | 7/2011 | Agan et al. |
| 2011/0275542 | A1 | 11/2011 | Eden et al. |
| 2011/0312534 | A1 | 12/2011 | Kayser et al. |
| 2013/0309168 | A1 | 11/2013 | Ho |
| 2014/0127827 | A1 | 5/2014 | Kim et al. |
| 2014/0206016 | A1 | 7/2014 | S?nchez et al. |
| 2014/0227324 | A1 | 8/2014 | Robinson et al. |
| 2015/0017630 | A1 | 1/2015 | Oved et al. |
| 2016/0153993 | A1 | 6/2016 | Eden et al. |
| 2017/0030909 | A1 | 2/2017 | Oved et al. |
| 2017/0234873 | A1 | 8/2017 | Oved et al. |
| 2017/0235871 | A1 | 8/2017 | Eden et al. |
| 2017/0269081 | A1 | 9/2017 | Oved et al. |
| 2018/0074057 | A1 | 3/2018 | Eden et al. |
| 2019/0011456 | A1 | 1/2019 | Oved et al. |
| 2019/0041388 | A1 | 2/2019 | Oved et al. |
| 2019/0085378 | A1 | 3/2019 | Eden et al. |
| 2019/0120837 | A1 | 4/2019 | Eden et al. |
| 2019/0161813 | A1 | 5/2019 | Oved et al. |
| 2019/0237156 | A1 | 8/2019 | Eden et al. |
| 2019/0242894 | A1 | 8/2019 | Oved et al. |
| 2019/0242895 | A1 | 8/2019 | Eden et al. |
| 2019/0339189 | A1 | 11/2019 | Takeda et al. |
| 2020/0088728 | A1 | 3/2020 | Oved et al. |
| 2020/0124593 | A1 | 4/2020 | Oved et al. |
| 2020/0388347 | A1 | 12/2020 | Eden et al. |
| 2020/0393463 | A1 | 12/2020 | Oved et al. |
| 2020/0400668 | A1 | 12/2020 | Eden et al. |
| 2022/0011320 | A1 | 1/2022 | Eden et al. |
| 2022/0042994 | A1 | 2/2022 | Oved et al. |

FOREIGN PATENT DOCUMENTS

| | | |
|---|---|---|
| CN | 101479389 | 7/2009 |
| CN | 101523217 | 9/2009 |
| CN | 101541976 | 9/2009 |
| CN | 101611314 | 12/2009 |
| CN | 101617056 | 12/2009 |
| CN | 101617230 | 12/2009 |
| CN | 101622364 | 1/2010 |
| CN | 101790687 | 7/2010 |
| CN | 102301002 | 12/2011 |
| CN | 103119444 | 5/2013 |
| CN | 104204803 | 12/2014 |
| CN | 105556308 | 5/2016 |
| EP | 1489416 | 12/2004 |
| JP | 2005-106694 | 4/2005 |
| JP | 2007-518062 | 7/2007 |
| JP | 2008-502908 | 1/2008 |
| JP | 2011-069696 | 4/2011 |
| KR | 10-2016-0072626 | 6/2016 |
| WO | WO 95/29404 | 11/1995 |
| WO | WO 99/33965 | 7/1999 |
| WO | WO 99/60171 | 11/1999 |
| WO | WO 01/14535 | 3/2001 |
| WO | WO 2004/108899 | 12/2004 |
| WO | WO2005/033327 | 4/2005 |
| WO | WO 2006/009702 | 1/2006 |
| WO | WO 2007/011412 | 1/2007 |
| WO | WO 2007/088355 | 8/2007 |
| WO | WO 2007/127801 | 11/2007 |
| WO | WO 2008/024642 | 2/2008 |
| WO | WO 2009/015821 | 2/2009 |
| WO | WO 2009/021521 | 2/2009 |
| WO | WO 2009/025743 | 2/2009 |
| WO | WO 2009/077864 | 6/2009 |
| WO | WO-2009100907 A1 * | 8/2009 |
| WO | WO 2009/130176 | 10/2009 |
| WO | WO 2009/158521 | 12/2009 |
| WO | WO 2010/056637 | 5/2010 |
| WO | WO 2011/008349 | 1/2011 |
| WO | WO 2011/017682 | 2/2011 |
| WO | WO 2011/132086 | 10/2011 |
| WO | WO 2013/117746 | 8/2013 |
| WO | WO 2014/006408 | 1/2014 |
| WO | WO 2014/049255 | 4/2014 |
| WO | WO 2014/117873 | 8/2014 |
| WO | WO 2015/048098 | 4/2015 |
| WO | WO 2016/024278 | 2/2016 |
| WO | WO 2016/059636 | 4/2016 |
| WO | WO 2016/079219 | 5/2016 |
| WO | WO 2016/092554 | 6/2016 |
| WO | WO 2017/149547 | 9/2017 |
| WO | WO 2017/149548 | 9/2017 |
| WO | WO 2017/221255 | 12/2017 |
| WO | WO 2018/011795 | 1/2018 |
| WO | WO 2018/011796 | 1/2018 |
| WO | WO 2018/060998 | 4/2018 |
| WO | WO 2018/060999 | 4/2018 |

OTHER PUBLICATIONS

Osmancik et al. Prognostic value of TNF-related apoptosis inducing ligand (TRAIL) in acute coronary syndrome patients. PLoS One 8(2): e53860, 2013.*

Volpato et al. Association of tumor necrosis factor-related apoptosis-inducing ligand with total and cardiovascular mortality in older adults. Atherosclerosis 215: 452-458, 2011.*

Bone et al. Definitions for sepsis and organ failure and guidelines for use of innovative therapies in sepsis. Chest 101(6): 1644-1655, 1992.*

Altmann et al. Elevated cardiac Troponin I in sepsis and septic shock: no evidence for thrombus associated myocardial necrosis. PLoS One 5(2): e9017, 2010.*

Ammann et al. Elevation of troponin I in sepsis and septic shock. Int Care Med 27: 965-969, 2001.*

Arshed et al. Elevated troponin I in the absence of coronary artery disease: a case report with review of literature. J Clin Med Res 7(10): 820-824, 2015.*

Bessiere et al. Prognostic value of troponins in sepsis: a meta-analysis. Int Care Med 39: 1181-1189, 2013.*

Gaedtke et al. Elevated troponin is associated with mortality in severe sepsis and septic shock. Am J Resp Crit Care Med 189: A3785, 2014.*

Sheyin et al. The prognostic significance of troponin elevation in patients with sepsis: a meta-analysis. Heart & Lung 44: 75-81, 2015.*

Wu et al. Increased troponin in patients with sepsis and septic shock: myocardial necrosis or myocardial depression? Int Care Med 27:959-961, 2001.*

(56) References Cited

OTHER PUBLICATIONS

Communication Pursuant to Article 94(3) EPC dated May 25, 2020 From the European Patent Office Re. Application No. 11748712.4. (7 Pages).
Official Action dated May 15, 2020 from the US Patent and Trademark Office Re. U.S. Appl. No. 16/238,582. (92 pages).
Official Action dated May 7, 2020 from the US Patent and Trademark Office Re. U.S. Appl. No. 16/157,193. (23 pages).
Supplementary European Search Report and the European Search Opinion dated May 4, 2020 From the European Patent Office Re. Application No. 17855163.6. (9 Pages).
Ali et al. "Reliability of Serum Procalcitonin Concentrations for the Diagnosis of Sepsis in Neonates", Egypt Journal of Immunology, 15(1): 75-84, 2008. Abstract only.
Becker et al. "Procalcitonin in Sepsis and Systemic Inflammation: a Harmful Biomarker and a Therapeutic Target", British Journal of Pharmacology, 159: 253-264, 2010.
Forde et al. "The Beneficial Pleiotropic Effects of Tumour Necrosis Factor-Related Apoptosis-Inducing Ligand (TRAIL) Within the Vasculature: A Review of the Evidence", Atherosclerosis, XP029468976, 247: 87-96, Available Online Feb. 9, 2016.
Herzig et al. "The Role of CXCL10 in the Pathogenesis of Experimental Septic Shock", Critical Care, 18(3): 1-18, 2014.
Ng et al. "IP-10 is an Early Diagnostic Marker for Identification of Late-Onset Bacterial Infection in Preterm Infants", Pediatric Research, 61(1): 93-98, 2007.
Povoa et al. "C-Reactive Protein, an Early Marker of Community-Acquired Sepsis Resolution: a Multi-Center Prospective Observational Study", Critical Care, 15(4): 1-10, 2011.
Sasaki et al. "Differentiating Between Bacterial and Viral Infection by Measuring Both C-Reactive Protein and 2'-5'-Oligoadenylate Synthetase as Inflammatory Markers", Journal of Infection and Chemotherapy, XP055696216, 8(1): 76-80, Mar. 2002.
Hearing Notice Dated Jul. 16, 2019 From the Government of India, Patent Office, Intellectual Property Building Re. Application No. 1780/MUMNP/2014. (3 Pages).
Notice of Allowance dated Jul. 29, 2019 From the US Patent and Trademark Office Re. U.S. Appl. No. 15/237,728. (21 pages).
Communication Pursuant to Article 94(3) EPC dated Mar. 25, 2020 From the European Patent Office Re. Application No. 18162713.4. (5 Pages).
Communication Pursuant to Article 94(3) EPC dated Mar. 27, 2020 From the European Patent Office Re. Application No. 15868614.7. (6 Pages).
Official Action dated Mar. 26, 2020 from the US Patent and Trademark Office Re. U.S. Appl. No. 16/687,726. (47 pages).
Official Action dated Mar. 31, 2020 from the US Patent and Trademark Office Re. U.S. Appl. No. 15/531,747. (21 pages).
Restriction Official Action dated Apr. 2, 2020 from the US Patent and Trademark Office Re. U.S. Appl. No. 16/081,069. (7 pages).
Greenspan et al. "Defining Epitopes: It's Not as Easy as It Seems", Nature Biotechnology, 17: 936-937, Oct. 1999.
Lloyd et al. "Modelling the Human Immune Response: Performance of a 1011 Human Antibody Repertoire Against a Broad Panel of Therapeutically Relevant Antigens", Protein Engineering, Design & Selection 22(3): 159-168, Oct. 29, 2008.
Rudikoff et al. "Single Amino Acid Substitution Altering Antigen-Binding Specificity", PNAS, 79(6): 1979-1983, Mar. 1982.
Office Action dated Nov. 28, 2019 From the Israel Patent Office Re. Application No. 254095 and Its Translation Into English. (7 Pages).
Restriction Official Action Dated Nov. 29, 2019 From the US Patent and Trademark Office Re. U.S. Appl. No. 16/238,582. (7 pages).
Translation of Reason for Rejection dated Nov. 21, 2019 of OA of Nov. 12, 2019 From the Japanese Patent Office Re. Application No. 2017-126712. (2 Pages).
Communication Pursuant to Article 94(3) EPC dated Nov. 12, 2020 From the European Patent Office Re. Application No. 17759389.4. (6 Page).
Official Action Dated Nov. 23, 2020 From the US Patent and Trademark Office Re. U.S. Appl. No. 16/355,984. (9 pages).
Notification of Office Action and Search Report dated Jul. 28, 2020 From the State Intellectual Property Office of the People's Republic of China Re. Application No. 201810781584.9 and Its Translation of Office Action Into English.
Bai et al. "A New Early Diagnostic Marker for Inflammatory Diseases—sTREM-1", International Journal of Pathology and Clinical Medicine, 27(1): 73-76, Feb. 2007.
Cai et al. "The Study on the Relationship Between PCT and CRP in Infective Diseases", Journal of Qiqihar University of Medicine, 32(5): 696-697, 2011.
Communication Pursuant to Article 94(3) EPC dated Jul. 31, 2019 From the European Patent Office Re. Application No. 18162713.4. (4 Pages).
Ludwig et al. "Tumor Necrosis Factor Related Apoptosis Inducing Ligand: A Novell Mechanism for Bacillus Calmette Guerin Induced Antitumc Research" Cancer Research 64: 3386-3390, May 15, 2004.
Communication Pursuant to Article 94(3) EPC dated May 7, 2019 From the European Patent Office Re. Application No. 15831781.8. (3 Pages).
Notification of Office Action dated Jun. 3, 2019 From the China National Intellectual Property Administration Re. Application No. 201610817276.8 and Its Translation Into English. (10 Pages).
Official Action dated Oct. 20, 2020 From the US Patent and Trademark Office Re. U.S. Appl. No. 16/081,069. (112 Pages).
ThermoFisher Scientific "Interferon Alpha Inducible Protein 27: IF127", ThermoFisher Scientific, Product Details, 2 P., 2020.
ThermoFisher Scientific "Interferon Induced Protein 44 Like: IF144L", ThermoFisher Scientific, Product Details, 2 P., 2020.
ThermoFisher Scientific "TaqMan Gene Expression Assay Solutions: Proven 5' Nuclease-Based Real-Time PCR Chemistry", Thermo Fisher Scientific, Applied Biosystems, 11 P., 2015.
Zaas et al. Supplementary Materials for "A Host-Based RT-PCR Gene Expression Signature to Identify Acute Respiratory Viral Infection", Science Translational Medicine, 5(203): 203ra126-1-203ra126-21, Sep. 18, 2013.
Examination Report dated May 29, 2019 From the Australian Government, IP Australia Re. Application No. 2018202302. (5 Pages).
Official Action dated Nov. 4, 2020 From the US Patent and Trademark Office Re. U.S. Appl. No. 16/238,582. (37 Pages).
Official Action dated Mar. 5, 2020 From the US Patent and Trademark Office Re. U.S. Appl. No. 15/713,722. (24 pages).
Applicant-Initiated Interview Summary dated Jul. 6, 2016 From the US Patent and Trademark Office Re. U.S. Appl. No. 14/377,887.
Applicant-Initiated Interview Summary dated Jul. 17, 2015 From the US Patent and Trademark Office Re. U.S. Appl. No. 13/090,893.
Applicant-Initiated Interview Summary dated Feb. 22, 2017 From the US Patent and Trademark Office Re. U.S. Appl. No. 14/377,887. (3 Pages).
Applicant-Initiated Interview Summary dated Oct. 26, 2017 From the US Patent and Trademark Office Re. U.S. Appl. No. 15/237,728. (3 pages).
Applicant-Initiated Interview Summary dated Jul. 30, 2018 From the US Patent and Trademark Office Re. U.S. Appl. No. 15/641,400. (3 pages).
Communication Pursuant to Article 94(3) EPC dated Dec. 9, 2016 From the European Patent Office Re. Application No. 13703112.6. (4 Pages).
Communication Pursuant to Article 94(3) EPC dated Oct. 9, 2018 From the European Patent Office Re. Application No. 11748712.4. (8 Pages).
Communication Pursuant to Article 94(3) EPC dated Jun. 17, 2016 From the European Patent Office Re. Application No. 11748712.4.
European Search Report and the European Search Opinion dated May 16, 2018 From the European Patent Office Re. Application No. 18162713.4. (7 Pages).
Examination Report dated Oct. 6, 2017 From the Australian Government, IP Australia Re. Application No. 2013217935. (2 Pages).
Examination Report Under Sections 12 & 13 of the Patents Act, 1970 and the Patents Rules, 2003 dated Mar. 26, 2018 From the

(56) References Cited

OTHER PUBLICATIONS

Government of India, Intellectual Property India, Patents, Designs, Trade Marks, Geographical Indications Re. Application No. 9122/DELNP/2012. (7 Pages).
Examination Report Under Sections 12 & 13 of the Patents Act, 1970 and the Patents Rules, 2003 dated Nov. 30, 2018 From the Government of India, Intellectual Property India, Patents, Designs, Trade Marks, Geographical Indications Re. Application No. 1780/MUMNP/2014. (7 Pages).
Examiner-Initiated Interview Summary dated Nov. 27, 2017 From the US Patent and Trademark Office Re. U.S. Appl. No. 15/518,491. (2 pages).
International Preliminary Report on Patentability dated Apr. 11, 2019 From the International Bureau of WIPO Re. Application No. PCT/IL2017/051088. (6 Pages).
International Preliminary Report on Patentability dated Apr. 11, 2019 From the International Bureau of WIPO Re. Application No. PCT/IL2017/051089. (7 Pages).
International Preliminary Report on Patentability dated Sep. 13, 2018 From the International Bureau of WIPO Re. Application No. PCT/IL2017/050270. (7 Pages).
International Preliminary Report on Patentability dated Sep. 13, 2018 From the International Bureau of WIPO Re. Application No. PCT/IL2017/050271. (9 Pages).
International Preliminary Report on Patentability dated Jun. 22, 2017 From the International Bureau of WIPO Re. Application No. PCT/IL2015/051201. (7 Pages).
International Preliminary Report on Patentability dated Feb. 23, 2017 From the International Bureau of WIPO Re. Application No. PCT/IL2015/050823. (7 Pages).
International Preliminary Report on Patentability dated Jan. 24, 2019 From the International Bureau of WIPO Re. Application No. PCT/IL2017/050780. (9 Pages).
International Preliminary Report on Patentability dated Jan. 24, 2019 From the International Bureau of WIPO Re. Application No. PCT/IL2017/050781. (7 Pages).
International Preliminary Report on Patentability dated Apr. 27, 2017 From the International Bureau of WIPO Re. Application No. PCT/IL2015/051024. (7 Pages).
International Search Report and the Written Opinion dated Mar. 12, 2012 From the International Searching Authority Re. Application No. PCT/IB2011/001299.
International Search Report and the Written Opinion dated Sep. 14, 2017 From the International Searching Authority Re. Application No. PCT/IL2017/050781. (12 Pages).
International Search Report and the Written Opinion dated Jun. 15, 2017 From the International Searching Authority Re. Application No. PCT/IL2017/050270. (13 Pages).
International Search Report and the Written Opinion dated Jun. 15, 2017 From the International Searching Authority Re. Application No. PCT/IL2017/050271. (16 Pages).
International Search Report and the Written Opinion dated Sep. 18, 2017 From the International Searching Authority Re. Application No. PCT/IL2017/050780. (15 Pages).
International Search Report and the Written Opinion dated Jan. 20, 2016 From the International Searching Authority Re. Application No. PCT/TL2015/051024.
International Search Report and the Written Opinion dated Feb. 22, 2016 From the International Searching Authority Re. Application No. PCT/IL2015/051201.
International Search Report and the Written Opinion dated Dec. 25, 2017 From the International Searching Authority Re. Application No. PCT/IL2017/051088. (9 Pages).
International Search Report and the Written Opinion dated Dec. 28, 2017 From the International Searching Authority Re. Application No. PCT/IL2017/051089. (10 Pages).
International Search Report and the Written Opinion dated Nov. 29, 2015 From the International Searching Authority Re. Application No. PCT/IL2015/050823.

International Search Report dated Apr. 5, 2013 From the International Searching Authority Re. Application No. PCT/EP2013/052619.
Notice of Allowance dated Feb. 4, 2019 From the US Patent and Trademark Office Re. U.S. Appl. No. 15/503,439. (6 pages).
Notice of Non-Compliant Amendment dated Aug. 4, 2015 From the US Patent and Trademark Office Re. U.S. Appl. No. 13/090,893.
Notice of Reasons for Rejection dated Nov. 1, 2016 From the Japan Patent Office Re. Application No. 2014-556086 and Its Translation Into English. (12 Pages).
Notice of Reasons for Rejection dated Apr. 2, 2019 From the Japan Patent Office Re. Application No. 2017-126712 and Its Translation Into English. (8 Pages).
Notice of Reasons for Rejection dated Jun. 19, 2018 From the Japan Patent Office Re. Application No. 2017-126712 and Its Translation Into English. (9 Pages).
Notice on Office Action and the Search Report dated Feb. 25, 2015 From the State Intellectual Property Office of the People's Republic of China Re. Application No. 201180030792.1 and Its Translation Into English.
Notification of Lack of Unity and Search Report dated Jan. 21, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (12 Pages).
Notification of Office Action and Search Report dated Mar. 4, 2016 From the State Intellectual Property Office of the People's Republic of China Re. Application No. 201380019055.0.
Notification of Office Action and Search Report dated Jan. 11, 2019 From the State Intellectual Property Office of the People's Republic of China Re. Application No. 201580055946.0. (5 Pages).
Notification of Office Action and Search Report dated Feb. 13, 2017 From the State Intellectual Property Office of the People's Republic of China Re. Application No. 201380019055.0 and Its Translation of Office Action Into English. (10 Pages).
Notification of Office Action and Search Report dated Feb. 19, 2019 From the State Intellectual Property Office of the People's Republic of China Re. Application No. 201580075265.0 and a Summary of the Notification of Office Action Into English.(7 Pages).
Notification of Office Action and Search Report dated Jun. 19, 2018 From the State Intellectual Property Office of the People's Republic of China Re. Application No. 201580075265.0 and its English Summary. (14 Pages).
Notification of Office Action and Search Report dated Oct. 30, 2017 From the State Intellectual Property Office of the People's Republic of China Re. Application No. 201610817276.8. (10 Pages).
Notification of Office Action dated Jul. 3, 2015 From the State Intellectual Property Office of the People's Republic of China Re. Application No. 201380019055.0.
Notification of Office Action dated Aug. 4, 2016 From the State Intellectual Property Office of the People's Republic of China Re. Application No. 201380019055.0 and Its Translation Into English.
Notification of Office Action dated May 6, 2014 From the State Intellectual Property Office of the People's Republic of China Re. Application No. 201180030792.1 and Its Translation Into English.
Notification of Office Action dated Jan. 21, 2016 From the State Intellectual Property Office of the People's Republic of China Re. Application No. 201180030792.1 and Its Translation Into English.
Notification of Office Action dated Aug. 25, 2017 From the State Intellectual Property Office of the People's Republic of China Re. Application No. 201380019055.0. (6 Pages).
Notification of Office Action dated Aug. 28, 2015 From the State Intellectual Property Office of the People's Republic of China Re. Application No. 201180030792.1 and Its Translation Into English.
Notification of Office Action dated Aug. 30, 2018 From the State Intellectual Property Office of the People's Republic of China Re. Application No. 201610817276.8 and Its Translation Into English. (22 Pages).
Notification of Reexamination dated Jan. 12, 2018 From the State Intellectual Property Office of the People's Republic of China Re. Application No. 2013800190and Its Machine Translation into English.

(56) References Cited

OTHER PUBLICATIONS

Office Action dated Feb. 18, 2019 From the Israel Patent Office Re. Application No. 250585 and Its Translation Into English. (6 Pages).
Office Action dated Jun. 20, 2018 From the State Intellectual Property Office of the People's Republic of China Re. Application No. 201580055946.0 and Its Summary of the Notification of Office Action Into English.).(5 Pages).
Office Action dated Feb. 29, 2016 From the Israel Patent Office Re. Application No. 233998 and Its Translation Into English.
Official Action dated Sep. 1, 2015 From the US Patent and Trademark Office Re. U.S. Appl. No. 13/090,893.
Official Action dated Apr. 4, 2016 From the US Patent and Trademark Office Re. U.S. Appl. No. 13/090,893.
Official Action dated Jan. 4, 2019 From the US Patent and Trademark Office Re. U.S. Appl. No. 151713,722. (72 pages).
Official Action dated Feb. 6, 2018 From the US Patent and Trademark Office Re. U.S. Appl. No. 15/503,439. (63 pages).
Official Action dated Nov. 7, 2016 From the US Patent and Trademark Office Re. U.S. Appl. No. 13/090,893. (26 pages).
Official Action dated Jun. 10, 2013 From the US Patent and Trademark Office Re. U.S. Appl. No. 13/090,893.
Official Action dated Apr. 12, 2018 From the US Patent and Trademark Office Re. U.S. Appl. No. 15/518,491. (59 pages).
Official Action dated Aug. 12, 2015 From the US Patent and Trademark Office Re. U.S. Appl. No. 14/377,887.
Official Action dated May 12, 2017 From the US Patent and Trademark Office Re. U.S. Appl. No. 15/237,728. (27 pages).
Official Action dated Apr. 13, 2016 From the US Patent and Trademark Office Re. U.S. Appl. No. 14/377,887.
Official Action dated Mar. 13, 2014 From the US Patent and Trademark Office Re. U.S. Appl. No. 13/090,893.
Official Action dated Apr. 15, 2019 From the US Patent and Trademark Office Re. U.S. Appl. No. 15/237,728. (16 Pages).
Official Action dated Dec. 15, 2016 From the US Patent and Trademark Office Re. U.S. Appl. No. 14/377,887. (22 pages).
Official Action dated May 15, 2018 From the US Patent and Trademark Office Re. U.S. Appl. No. 15/237,728. (55 pages).
Official Action dated Nov. 16, 2018 From the US Patent and Trademark Office Re. U.S. Appl. No. 15/503,439. (41 pages).
Official Action dated Dec. 17, 2018 From the US Patent and Trademark Office Re. U.S. Appl. No. 15/237,728. (39 pages).
Official Action dated Nov. 18, 2016 From the US Patent and Trademark Office Re. U.S. Appl. No. 15/237,728. (33 pages).
Official Action dated Apr. 23, 2019 From the US Patent and Trademark Office Re. U.S. Appl. No. 16/157,193. (47 pages).
Official Action dated Jan. 26, 2017 From the US Patent and Trademark Office Re. U.S. Appl. No. 15/015,309. (45 pages).
Official Action dated Mar. 26, 2015 From the US Patent and Trademark Office Re. U.S. Appl. No. 13/090,893.
Official Action dated Apr. 30, 2018 From the US Patent and Trademark Office Re. U.S. Appl. No. 15/641,400. (62 pages).
Official Action dated Mar. 30, 2018 From the US Patent and Trademark Office Re. U.S. Appl. No. 15/531,747. (67 pages).
Requisition by the Examiner dated Nov. 9, 2018 From the Innovation, Science and Economic Development Canada, Canadian Intellectual Property Office Re. Application No. 2,796,666. (3 Pages).
Requisition by the Examiner dated Jan. 18, 2018 From the Innovation, Science and Economic Development Canada, Canadian Intellectual Property Office Re. Application No. 2,796,666. (5 Pages).
Requisition by the Examiner dated Feb. 21, 2019 From the Innovation, Science and Economic Development Canada, Canadian Intellectual Property Office Re. Application No. 2,863,819. (8 Pages).
Restriction Official Action dated Nov. 2, 2017 From the US Patent and Trademark Office Re. U.S. Appl. No. 15/531,747. (9 pages).
Restriction Official Action dated Nov. 8, 2018 From the US Patent and Trademark Office Re. U.S. Appl. No. 16/157,193. (5 pages).
Restriction Official Action dated May 10, 2018 From the US Patent and Trademark Office Re. U.S. Appl. No. 15/713,722. (6 Pages).
Restriction Official Action dated Feb. 13, 2013 From the US Patent and Trademark Office Re. U.S. Appl. No. 13/090,893.
Restriction Official Action dated May 15, 2015 From the US Patent and Trademark Office Re. U.S. Appl. No. 14/377,887.
Restriction Official Action dated Aug. 31, 2017 From the US Patent and Trademark Office Re. U.S. Appl. No. 15/518,491. (6 pages).
Search Report dated May 6, 2014 From the State Intellectual Property Office of the People's Republic of China Re. Application No. 201180030792.1 and Its Translation Into English.
Second Notice of Allowance dated Dec. 12, 2018 From the US Patent and Trademark Office Re. U.S. Appl. No. 15/641,400. (7 pages).
Supplementary European Search Report and the European Search Opinion dated Mar. 15, 2018 From the European Patent Office Re. Application No. 15831781.8. (11 Pages).
Supplementary European Search Report and the European Search Opinion dated Sep. 17, 2018 From the European Patent Office Re. Application No. 15868614.7. (18 Pages).
Supplementary Partial European Search Report and the European Provisional Opinion dated Jun. 1, 2018 From the European Patent Office Re. Application No. 15868614.7. (23 Pages).
Translation Dated Sep. 4, 2017 of Notification of Office Action dated Aug. 25, 2017 From the State Intellectual Property Office of the People's Republic of China Re. Application No. 201380019055.0.
Translation Dated Apr. 5, 2016 of Notification of Office Action dated Mar. 4, 2016 From the State Intellectual Property Office of the People's Republic of China Re. Application No. 201380019055.0.
Translation Dated Mar. 20, 2019 of Notification of Office Action dated Feb. 19, 2019 From the State Intellectual Property Office of the People's Republic of China Re. Application No. 201580075265.0. (5 Pages).
Translation Dated Sep. 21, 2015 of Office Action dated Jul. 3, 2015 From the State Intellectual Property Office of the People's Republic of China Re. Application No. 201380019055.0.
Translation of Notification dated Jan. 30, 2019 from OA of Jan. 11, 2019 From the State Intellectual Property Office of the People's Republic of China Re. Application No. 201580055946.0.(1 Page).
Translation of Notification of Office Action and Search Report dated Oct. 30, 2017 From the State Intellectual Property Office of the People's Republic of China Re. Application No. 201610817276.8. (16 Pages).
Alexander et al. "*Staphylococcus aureus* and *Salmonella enterica* Serovar Dublin Induce Tumor Necrosis Factor-Related Apoptosis-Inducing Ligand Expression by 1\1ormal Mouse and Hurnan Osteoblasts", Infection and Immunity, 69(3): 1581-1586, Mar. 2001.
Biezeveld et al. "Sustained Activation of Neutrophils in the Course of Kawasaki Disease: An Association with Matrix Metalloproteinases", Clinical & Experimental Immunology 141(1): 183-188, Jul. 2005.
Boldrick et al. "Stereotyped and Specific Gene Expression Programs in Human Innate Immune Responses to Bacteria", Proc. Natl. Acad. Sci. USA, PNAS, 99(2): 972-977, Jan. 22, 2002.
Borjesson et al. "Insights Into Pathogen Immune Evasion Mechanisms: Anaplasma Phagocytophilum Fails to Induce an Apoptosis Differentiation Program in Human Neutrophils", The Jurnal of Immunology, 174: 6364-6372, 2005.
Boser et al. "A Training Algorithm for Optimal Margin Classifiers", Proceedings of the 5th Annual ACM Workshop on Computational Learning Theory, COLT'92, Pittsburgh, PA, USA, Jul. 27-29, 1992, p. 144-152, Jul. 27, 1992.
Calvano et al. "A Network-Based Analysis of Systemic Inflammation in Humans", Nature, 437: 1032-1037, Oct. 13, 2005.
Carrol et al. "The Diagnostic and Prognostic Accuracy of Five Markers of Serious Bacterial Infection in Malawian Children With Sign of Severe Infection", PLoS ONE, 4(8): e6621-1-e6621-8, Aug. 2009.
Chagan-Yasutan et al. "Persistent Elevation of Plasma Osteopontin Levels in HIV Patients Despite Highly Active Antiretroviral Therapy", The Tohoku Journal of Experimental Medicine, 218(4): 285-292, Aug. 2009.
Chaussabel et al. "Analysis of Significance Patterns Identifies Ubiquitous and Disease-Specific Gene-Expression Signatures in

(56) References Cited

OTHER PUBLICATIONS

Patient Peripheral Blood Leukocytes", Annals of the New York Academy of Sciences, 1062: 146-154, 2005.
Chen et al. "Discordant Protein and mRNA Expression in Lung Adenocarcinomas", Molecular & Cellular Proteomics: MCP, 1(4): 304-313, Apr. 2002.
Chieux et al. "MxA Protein in Capillary Blood of Children With Viral Infections", Journal of Medical Virology, 59: 547-551, 1999.
Chieux et al. "The MxA Protein Levels in Whole Blood Lysates of Patients With Various Viral Infections", Journal of Virological Methods, 70: 183-191, 1998.
Corada et al. "Monoclonal Antibodies Directed to Different Regions of Vascular Endothelial Cadherin Extracellular Domain Affect Adhesion and Clustering of the Protein and Modulate Endothelial Permeability", Blood, 97(6): 1679-1684, Mar. 15, 2001.
Cowland et al. "Molerular Charaderization and Pattern of Tissue Expression of the Gene for Neutrophil Gelatinase-Associated Upocalin from Humans", Genomics, 45:17-23,1997.
Cristianini et al. "An Introduction to Support Vector Machines and Other Kernel-Based Learning Methods: Contents", Cambridge University Press, 4 P., 2000.
Crowe et al. "Quantitative Immunocytofluorographic Analysis of CD4 Surface Antigen Expression and HIV Infection of Human Peripheral Blood Monocyte/Macrophages", Aids Research and Human Retroviruses, 3(2): 135-145, 1987.
Cummins et al. "The TRAIL to Viral Pathogenesis: The Good, the Bad and the Ugly", Current Molecular Medicine, XP055056835, 9(4): 495-505, May 1, 2009.
Dirke et al. "TRAIL and DcR1 Expressions are Differentially Regulated in the Pancreatic Islets of STZ-Versus CY-AppHed NOD Mice", Experimental Diabetes Research, Article ID 625813, pp. 1-11, 2011.
Duda et al. "Contents", Pattern Classification, 2nd Ed., 11 P., 2001.
Eberl et al. "A Rapid Crosstalk of Human ?? T Cells and Monocytes Drives the Acute Inflammation in Bacterial Infections", PLOS Pathogens 5(2): 1-16, 2009.
Falschlehner et al. "Following TRAIL'S Path in the Immune System", Immunology, XP055056763, 127(2): 145-154, Jun. 1, 2009. Chapter 'TRAIL in Viral and Bacterial Infections'.
Feezor et al. "Molecular Characterization of the Acute Inflammatory Response to Infections With Gram-Negaitve Versus Gram-Positive Bacteria", Infection and Immunity, 71(10): 5803-5813, Oct. 2003.
Furey et al. "Support Vector Machine Classification and Validation of Cancer Tissue Samples Using Microarray Expression Data", Bioinformatics, 16(10): 906-914, Oct. 2000.
Halminen et al. "Expression of MxA Protein in Blood Lymphocytes Discriminates Between Viral and Bacterial infections in Febrile Children", Pediatric Research, 41(5): 647-650, May 1997.
Hanley et al. "A Method of Comparing the Areas Under Receiver Operating Characteristics Curves Derived From the Same Cases", Radiology, 148(3): 839-843, Sep. 1983.
Hastie et al. "The Elements of Statistical Learning: Data Mining, Inference, and Prediction", Springer Series in Statistics, 2nd Ed., p. 1-745, 2001.
Hinson et al. "Viperin is Highly Induced in Neutrophils and Macrophages during Acute and Chronic Lymphocytic Choriomeningitis Virus Infection", The Journal of Immunology, 184:5723-5731, 2010.
Hoffmann et al. "TRAIL Limits Excessive Host Immune Responses in Bacterial Meningitis", JCI the Journal of Clinical Investigation. 117(7): 2004-2013, Jul. 2, 2007.
Holland et al. "STAT3 Mutations in the Hyper-IgE Syndrome", The New England Journal of Medicine, 357(16): 1608-1619, Oct. 18, 2007.
Janols et al. "Lymphocyte and Monocyte Flow Cytometry Immunophenotyping as a Diagnostic Tool in Uncharacteristic Inflammatory Disorders", BMC Infectious Diseases, XP002663504, 10(205): 1-9, 2010. Abstract.
Jenner et al. "Insights Into Host Responses Against Pathogens From Transcriptional Profiling", Nature Review Microbiology, 3: 281-294, Apr. 2005.
Kaizer et al. "Gene Expression in Peripheral Blood Mononuclear Cells From Children With Diabetes", The Journal of Clinical Endocrinology & Metabolism, 92(9): 3705-3711,2007.
Kawada et al. "Analysis of Gene-Expression Profiles by Oligonucleotide Microarray in Children With Influenza", Journal of General Virology, 87: 1677-1683, 2006.
Kichev et al. "Tumor Necrosis Factor-Related Apoptosis-Inducing Ligand (TRAiL) Signaling and Cell Death in the Immature Central Nervous System after Hypoxia-Ischemia and Inflammation", Journal of Biological Chemistry 289(13): 9430-9439, 2014.
Kohavi et al. "Wrappers for Feature Subset Selection", Artifical Intelligence, 97: 273-324, 1997.
Kotelkin et al. "Respiratorv Syncytial Virus Infections Sensitizes Cells to Apoptosis Mediated by Tumor Necrosis Factor-Related Apoptosis-Inducing Ligand", Journal of Virology, XP055056816, 77(17): 9156-9172, Aug. 12, 2003. Fig.5B.
Lampe et al. "Expression of the Interferon-Induced MxA Protein in Viral Encephalitis", Neuropathology and Applied Neurobiology, 29(3): 273-279, May 27, 2003.
Le Roux "Les Examens a Visee Etiologique Dans les Pneumopathies Communautaires de l'Enfant (Hors Imagerie) [Laboratory Investigations in Acute Lower Respiratory Tract Infections in Children]", Archives de Pediatrie, XP002663501,5(Suppl.1): 28S-32S, 1998. Abstract.
Leibovici et al. "The Benefit of Appropriate Empirical Antibiotic Treatment in Patients with Bloodstream Infection", Journal of Internal Medicine, 244(5): 379-386, Nov. 1, 1998.
Liabeuf et al. "The Circulating Soluble TRAII, Is a Negative Marker for Inflammation Inversely Associated With the Mortality Risk in Chronic Kidney Disease Patients", Nephrology Dialysis Transplantation, 25(8): 2596-2602, Advance Access Publication Feb. 26, 2010. Abstract, p. 2597, Right col. 2nd Para, Figs.2, 3.
Liu et al. "Early Days: Genomics and Human Responses to Infection", Current Opinion in Microbiology, 9: 312-319, Available Online May 6, 2006.
Malcolm et al. "Microarrays Analysis of Lipopolysaccharide-Treated Human Neutrophils", American Journal of Physiology, Lung Cellular & Molecular Physiology, 284(4): L663-L670, First Published Dec. 20, 2002.
Mount "Bioinformatics: Sequence and Genome Analysis", Chaps. 1-10: 1-564, 2001.
Nakabayashi et al. "MxA-Based Recognition of Viral Illness in Febrile Children by a Whole Blood Assay", Pediatric Research, 60(6): 770-774, 2006.
Neu et al. "Expression of Tumor Necrosis Factor-Alpha-Related Apoptosis-Inducing Ligand and Its Proapoptotic Receptors is Down-Regulated during Gastric Infection with Virulent cagA+/vacAsl+ Helicobacter pylori Strains", The Journal of Infectious Diseases 191(4): 571-578, Feb. 15, 2005.
Niederman "Biological Markers to Determine Eligibility in Trials for Community-Acquired Pneumonia: A Focus on Procalcitonin", Clinical Infectious Diseases, XP002670357, 47(Suppl.3): S127-S132, Dec. 2008.
Niessner et al. "Prognostic Value of Apoptosis Markers in Advanced Heart Failure Patients", European Heart Journal, 30(7): 789-796, Published Online Feb. 4, 2009. Abstract, Table 2, Fig.2.
Oda et al. "A Comprehensive Map of the Toll-Like Receptor Signaling Network", Molecular Systems Biology, 2(2006.0015): 1-20, Apr. 18, 2006.
Oved et al. "A Novel Host-Proteome Signature for Distinguishing Between Acute Bacterial and Viral Infections", PLOS ONE, 10(3): e0120012-1-e120012-18, Mar. 18, 2015. Figs.3C, 4.
Padlan "X-Ray Crystallography of Antibodies", Advances in Protein Chemistry, 49: 57-133; 1996.
Paul et al. "Systematic Review and Meta-Analysis of the Efficacy of Appropriate Empiric Antibiotic Therapy for Sepsis", Antimicrobial Agents and Chemotherapy, 54(11): 4851-4863, Nov. 2010.
Radom-Aizik et al. "Effects of 30 Min. of Aerobic Exercise on Gene Expression in Human Neutrophils", Journal of Applied Physiology, 104: 236-243, 2008.

(56) References Cited

OTHER PUBLICATIONS

Ramilo et al. "Gene Expression Patterns in Blood Leukocytes Discriminate Patients With Acute Infections", Blood, 109(5): 2066-2077, Mar. 1, 2007.
RayBiotech "Mouse L308 Array, Membrane [AAM-BLM-1]1-Series-308-Label-Based-Mouse-Cytok", RayBiotech, XP055473187, Retrieved From the Internet, 7 P., May 7, 2018.
Rosseau et al. "Comparative Transcriptional Profiling of the Lung Reveals Shared and Distinct Features of *Streptococcus pneumoniae* and Influenza A Virus Infection", Immunology, 120: 380-391, 2006.
Secchiero et al. "Potential Prognostic Significance of Decreased Serum Levels of TRAIL After Acute Myocardial Infarction", PLoS ONE. XP055056988, 4(2): e4442-1-e4442-6, Feb. 16, 2009. Fig.1.
Shimetani et al. "Levels of Three Inflammation Markers, C-Reactive Protein, Serum Amyloid A Protein and Procalcitonin, in the Serum and Cerebrospinal Fluid of Patients With Meningitis", Scandinavian Journal of Clinical and Laboratory Investigation, XP008113027, 61(7): 567-574, 2001. Abstract.
Singer et al. "The Third International Consensus Definitions for Sepsis and Septic Shock (Sepsis-3)", Journal of the American Medical Association, JAMA, 315(8): 801-810, Feb. 23, 2016. Box 3, Fig.
Smith et al. "Quantitative Assessment of Human Whole Blood RNA as a Potential Biomarker for Infectious Disease", Analyst, 132: 1200-1209, First Published Oct. 31, 2007.
Sukumaran et al. "Early Transcriptional Response of Human Neutrophils to Anaplasma Phagocytophilum Infection", Infection and Immunity, 73(12): 8089-8099, Dec. 1, 2005.
Sullivan Pepe et al. "Combining Diagnostic Test Results to Increase Accuracy", Biostatistics, XP055033234, 1(2): 123-140, Jun. 1, 2000. Abstract, Section 2.4.
Tang et al. "Gene-Expression Profiling of Gram-Positive and Gram-Negative Sepsis in Critically Ill Patients", Critical Care Medicine, 36(4): 1125-1128, 2008.
Tang et al. "Hypoxic Preconditioning Enhances the Benefit of Cardiac Progenitor Cell Therapy for Treatment of Myocardial Infarction by Inducing CXCR4 Expression", Circulation Research, XP055473182, 104(10): 1209-1216, May 22, 2009. Online Table 1.
Tang et al. "The Use of Gene-Expression Profiling to Identify Candidate Genes in Human Sepsis", American Journal of Respiratory and Critical Care Medicine, 176: 676-684, Originally Published Jun. 15, 2007.
Thivierge et al. "Eukaryotic Elongation Factor 1A Interacts With Turnip Mosaic Virus RNA-Dependent RNA Polymerase and VPg-Pro in Virus-Induced Vesicles", Virology, XP002663503, 377(1): 216-225, Jul. 2008. Abstract, p. 220, r-h col. Para 3-p. 222, r-h col. Para 1.
Tian et al. "Soluble Tumor Necrosis Factor Related Apoptosis Inducing Ligand Level as a Predictor of Severity of Sepsis and the Risk of Mortality in Septic Patients", PLOS One, 8(12): e82204-1-e82204-5, Dec. 12, 2013. 'Study Design' Para, 'Inclusion Criteria' Para, Table 1, Figs.1, 3, Abstract, Table 1.
Tisato et al. "Low Circulating TRAIL Levels are Associated with Increase of Resistin and Lipocalin-2/ngal Adipokines in Postmenopausal Women", Mediators of Inflammation, Article ID 5356020, 8 Pages, 2017.
Torkkola "Feature Extraction by Non-Parametric Mutual Information Maximization", Journal of Machine Learning Research, 3: 1415-1438, Mar. 2003.
Tsuji "TRAILing Gastrointestinal Pathogenesis", Journal of Gastroenterology and Hepatology, 18(7): 753-755, Published Online Jun. 10, 2003.
Tworoger et al. "Collection, Processing, and Storage of Biological Samples in Epidemiologic Studies: Sex Hormones. Carotenoids, Inflammatory Markers, and Proteomics as Examples", Cancer Epidemiol Biomarkers and Prevention, 15(9): 1578-1581, Sep. 2006.
Vapnik "Statistical Learning Theory", Adaptive and Learning Systems for Signal Processing, Communications, and Control, p. 1-732, 1998.—Part I.
Vapnik "Statistical Learning Theory", Adaptive and Learning Systems for Signal Processing, Communications, and Control, p. 1-732, 1998.—Part II.
Vapnik "Statistical Learning Theory", Adaptive and Learning Systems for Signal Processing, Communications, and Control, p. 1-732, 1998. - PART III.
Vapnik "Statistical Learning Theory", Adaptive and Learning Systems for Signal Processing, Communications, and Control, p. 1-732, 1998. - Part Iv.
Vogel et al. "Sequence Signatures and mRNA Concentration Can Explain Two-Thirds of Protein Abundance Variation in A Human Cell Line", Molecular Systems Biology, 6(Art.400): 1-9, Published Online Aug. 24, 2010.
Wang et al. "Rotavirus Infection Alters Peripheral T-Cell Homeostasis in Children With Acute Diarrhea", Journal of Virology, 81(8): 3904-3912, Apr. 2007.
Whiteside et al. "Role of Human Natural Killer Cells in Health and Disease", Clinical and Diagnostic Laboratory Immunology, 1(2): 125-133, Mar. 31, 1994.
Xu et al. "Lipocalins as Biochemical Markers of Disease", Biochimica et Biophysica Acta, XP002376345, 1482(1): 298-307, Oct. 18, 2000. Abstract, Sections 3, 5, p. 303, col. 2 - p. 304, col. l, Bridging Para, p. 304, cols. 1-2, Bidging Para, Fig.l, Table 1.
Yamaji et al. "Significance of Eukaryotic Translation Elongation Factor 1A in Tobacco Mosaic Virus Infection", Archives of Virology, XP002663502, 155(2): 263-268, Feb. 2010. Abstract.
Yeung et al. "Serum Cytokines in Differentiating Between Viral and Bacterial Enterocolitis", Annals of Tropical Paediatrics, 24(4): 337-343, Published Online Jul. 18, 2013.
Zaas et al. "A Host-Based RT-PCR Gene Expression Signature to Identify Acute Respiratory Viral Infection", Science Translational Medicine, 5(203): 203ra126-1 -203ra126-19, Sep. 18, 2013.
Zaas et al. "Gene Expression Signatures Diagnose Influenza and Other Symptomatic Respiratory Viral Infections in Humans", Cell Host & Microbe, XP002670360, 6(3): 207-217, Sep. 17, 2009. Abstract, p. 212,1-h col. p. 213, 1-h col. Fig.4.
Zhu et al. "Use of Differential Display Analysis to Assess the Effect of Human Cytomegalovirus Infection on the Accumulation of Cellular RNAs: Induction of Interferon-Responsive RNAs", Proc. Natl. Acad. Sci. USA, XP002088235, 94(25): 13985-13990, Dec. 9, 1997. Abstract, Fig.2.
Zilliox et al. "Gene Expression Changes in Peripheral Blood Mononuclear Cells During Measles Virus Infection", Clinical and Vaccine Immunology, 14(7): 918-923, Jul. 2007.
Notice of Reason for Rejection dated Aug. 20, 2019 From the Japan Patent Office Re. Application No. 2017-507867 and Its Translation Into English. (5 Pages).
Office Action dated Jul. 30, 2020 From the Israel Patent Office Re. Application No. 261529 and Its Translation Into English. (5 Pages).
Office Action dated Jul. 30, 2020 From the Israel Patent Office Re. Application No. 261530 and Its Translation Into English. (5 Pages).
Restriction Official Action dated Jul. 30, 2020 from the US Patent and Trademark Office Re. U.S. Appl. No. 16/081,906. (7 pages).
Search Report and Opinion dated Aug. 20, 2019 From the Servigo Publico Federal, Ministerio da Economia, Institute National da Propriedade Industrial do Brasil Re. Application No. BRI 12014 019733-4 and Its Summary in English. (4 Pages).
Translation Dated Sep. 11, 2019 of Notification of Office Action dated Aug. 22, 2019 From the State Intellectual Property Office of the People's Republic of China Re. Application No. 201580055946. 0. (1 Page).
Applicant-Initiated Interview Summary dated Feb. 10, 2020 From the US Patent and Trademark Office Re. U.S. Appl. No. 16/157,193. (3 pages).
Supplementary European Search Report and the European Search Opinion dated Feb. 18, 2020 From the European Patent Office Re. Application No. 17827121.9. (5 Pages).
Official Action dated Feb. 3, 2020 From the US Patent and Trademark Office Re. U.S. Appl. No. 16/355,984. (24 pages).
Search Report and Opinion dated Dec. 10, 2019 From the Servico Publico Federal, Ministerio da Economia, Instituto National da Propriedade Industrial do Brasil Re. Application No. BRI 12017002884-0 and Its Translation Into English. (7 Pages).

(56) References Cited

OTHER PUBLICATIONS

Supplementary European Search Report and the European Search Opinion dated Jan. 21, 2020 From the European Patent Office Re. Application No. 17827122.7.
Official Action dated Oct. 15, 2019 From the US Patent and Trademark Office Re. U.S. Appl. No. 151713,722. (57 Pages).
Official Action dated Sep. 16, 2019 From the US Patent and Trademark Office Re. U.S. Appl. No. 16/355,984. (44 pages).
Official Action dated Sep. 18, 2019 From the US Patent and Trademark Office Re. U.S. Appl. No. 16/157,193. (30 pages).
Official Action dated Oct. 24, 2019 From the US Patent and Trademark Office Re. U.S. Appl. No. 15/531,747. (37 Pages).
Requisition by the Examiner dated Oct. 4, 2019 From the Innovation, Science and Economic Development Canada, Canadian Intellectual Property Office Re. Application No. 2,863,819. (3 Pages).
Supplementary European Search Report and the European Search Opinion dated Sep. 30, 2019 From the European Patent Office Re. Application No. 17759388.6. (11 Pages).
Supplementary Partial European Search Report and the European Provisional Opinion dated Oct. 24, 2019 From the European Patent Office Re. Application No. 17759389.4. (15 Pages).
Translation Dated Sep. 22, 2019 of Search Report and Opinion dated Aug. 20, 2019 From the Servi?o Publico Federal, Ministerio da Economia, Institute Nacional da Propriedade Industrial do Brasil Re. Application No. BR112014 019733-4 and Its Summary in English. (4 Pages).
Barnhart et al. "Changes in Cellular mRNA Stability, Splicing, and Polyadenylation Through HuR Protein Sequestration by a Cytoplasmic RNA Virus", Cell Reports, XP055621573, 5(4): 909-917, Nov. 27, 2013.
Consiglio et al. "BEAT: Bioinformatics Exon Array Tool to Store, Analyze and Visualize Affymetrix GeneChip Human Exon Array Data From Disease Experiments", BMC Bioinformatics, XP021117755, 13(Suppl.4): S21-1-S21-14, Mar. 28, 2012.
UCSC "UCSC Browser on Human Feb. 2009 (GRCh37/hgl9) Assembly: Showing Location of Probes on the Affymetrix ExonChip Binding to Exons of ANKRD22", Ucsc Browser, XP055621243, Retrieved From the Internet, 7 P., Jan. 2009.
UCSC "UCSC Genome Browser on Human Feb. 2009 (GRCh37/hg19) Assembly: Showing Location of Probes on the Affymetrix ExonChip Binding to Exons of AIM2", UCSC Browser, XP055621240, Retrieved From the Internet, 8 P., Jan. 2009.
Zaas et al. "The Current Epidemiology and Clinical Decisions Surrounding Acute Respiratory Infections", Trends in Molecular Medicine, XP055522333, 20(10): 579-588, Published Online Sep. 5, 2014.
Communication Pursuant to Article 94(3) EPC dated Jun. 4, 2020 From the European Patent Office Re. Application No. 17759388.6. (3 Pages).
Supplementary European Search Report and the European Search Opinion dated May 18, 2020 From the European Patent Office Re. Application No. 17855164.4. (13 Pages).
Shommu et al. "Metabolomic and Inflammatory Mediator Based Biomarker Profiling as a Potential Novel Method to Aid Pediatric Appendicitis Identification", PLOS ONE, XP055692841, 13(3): e0193563-1-e0193563-13, Mar. 12, 2018.
Notification of Office Action dated Jul. 2, 2019 From the State Intellectual Property Office of the People's Republic of China Re. Application No. 201580075265.0. (3 Pages).
Request for Examination dated Jun. 18, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (11 Pages).
Translation Dated Jul. 10, 2019 of Notification of Office Action dated Jul. 2, 2019 From the State Intellectual Property Office of the People's Republic of China Re. Application No. 201580075265.0. (1 Page).

Ju et al. "Research Progress of Some Inflammatory Markers in Infectious Diseases", Chinese Journal of Practical Internal Medicine, 30(Suppl.1): 80-81, Jun. 2010. With an English Translation.
Supplementary European Search Report and the European Search Opinion dated Jan. 28, 2020 From the European Patent Office Re. Application No. 17759389.4. (11 Pages).
Communication Pursuant to Article 94(3) EPC dated Sep. 25, 2020 From the European Patent Office Re. Application No. 17827122.7. (5 Pages).
European Search Report and the European Search Opinion dated Sep. 28, 2020 From the European Patent Office Re. Application No. 20164056.2. (10 Pages).
Interview Summary dated Oct. 14, 2020 from the US Patent and Trademark Office Re. U.S. Appl. No. 16/081,906. (3 pages).
Examination Report Under Sections 12 & 13 of the Patents Act, 1970 and the Patents Rules, 2003 dated Oct. 21, 2019 From the Government of India, Intellectual Property India, Patents. Designs, Trade Marks, Geographical Indications Re. Application No. 9122/DELNP/2012 (5 Pages).
Notice of Reason for Rejection dated Nov. 12, 2019 From the Japan Patent Office Re. Application No. 2017-126712 and an English Summary. (3 Pages).
Advisory Action Before the Filing of An Appeal Brief dated Dec. 23, 2019 From the US Patent and Trademark Office Re. U.S. Appl. No. 16/157,193. (3 pages).
Final Official Action dated Sep. 8, 2020 from the US Patent and Trademark Office Re. U.S. Appl. No. 16/687,726. (28 pages).
Restriction Official Action dated Sep. 10, 2020 from the US Patent and Trademark Office Re. U.S. Appl. No. 16/316,631. (6 pages).
Restriction Official Action dated Dec. 5, 2019 From the US Patent and Trademark Office Re. U.S. Appl. No. 16/081,906. (9 pages).
Partial European Search Report and Provisional Opinion dated Jun. 25, 2020 From the European Search Report Re. Application No. 20164056.2. (11 Pages).
Pepe et al. "Combining Diagnostic Test Results to Increase Accuracy", Biostatistics, XP055033234, 1(2): 123-140, Jun. 2000.
Communication Pursuant to Article 94(3) EPC dated Aug. 18, 2020 From the European Patent Office Re. Application No. 11748712.4. (3 Pages).
Patent Examination Report dated Feb. 8, 2021 From the Australian Government, IP Australia Re. Application No. 2015302870. (4 Pages).
Notification of Office Action and Search Report dated Feb. 20, 2021 From the State Intellectual Property Office of the People's Republic of China Re. Application No. 201780014568.0. (9 Pages).
Requisition by the Examiner dated Dec. 7, 2020 From the Innovation, Science and Economic Development Canada, Canadian Intellectual Property Office Re. Application No. 2,863,819. (4 Pages).
Restriction Official Action dated Dec. 9, 2020 from the US Patent and Trademark Office Re. U.S. Appl. No. 16/336,528. (7 pages).
Notice of Reasons for Rejection dated Apr. 20, 2021 From the Japan Patent Office Re. Application No. 2020-021606 and Its Translation Into English. (9 Pages).
Official Action dated May 5, 2021 From the US Patent and Trademark Office Re. U.S. Appl. No. 16/336,528. (108 Pages).
Brest et al. "Differential Expression of the TRAIL/TRAIL-receptor System in Patients with Inflammatory Bowel Disease", Pathology—Research and Practice, 206(1):43-50, Jan. 15, 2010.
Notification of Office Action dated Mar. 5, 2021 From the State Intellectual Property Office of the People's Republic of China Re. Application No. 201810781584.9 and Its Translation of Office Action Into English. (13 Pages).
Official Action dated Mar. 10, 2021 From the US Patent and Trademark Office Re. U.S. Appl. No. 16/081,906. (127 Pages).
Shair et al. "Epstein-Barr Virus Latent Membrane Protein-1 Effects on Junctional Plakoglobin and Induction of a Cadherin Switch", Cancer Research, Cell, Tumor, and Stem Cell Biology, 69(14): 5734-5742, Jul. 15, 2009.
Interview Summary dated Feb. 1, 2021 From the US Patent and Trademark Office Re. U.S. Appl. No. 16/687,726. (2 Pages).
Examination Report Under Sections 12 & 13 of the Patents Act, 1970 and the Patents Rules, 2003 dated Mar. 31, 2021 From the Government of India, Intellectual Property India, Patents, Designs,

(56) References Cited

OTHER PUBLICATIONS

Trade Marks, Geographical Indications, The Patent Office Re. Application No. 201727005513. (7 Pages).
Notice of Allowance dated Apr. 19, 2021 from the US Patent and Trademark Office Re. U.S. Appl. No. 16/238,582. (22 pages).
Bloos et al. "Rapid Diagnosis of Sepsis"; Virulence, 5(1): 154-160, 2014.
Henriquez-Camacho et al. "Biomarkers for Sepsis"; BioMed Research International, 547818: 6 pages, 2014.
Official Action dated Mar. 9, 2021 From the US Patent and Trademark Office Re. U.S. Appl. No. 16/316,631. (121 Pages).
Restriction Official Action dated Mar. 29, 2021 From the US Patent and Trademark Office Re. U.S. Appl. No. 16/081,069. (8 Pages).
Communication Pursuant to Article 94(3) EPC dated Mar. 17, 2021 From the European Patent Office Re. Application No. 15868614.7. (5 Pages).
Advisory Action dated Dec. 20, 2021 from US Patent and Trademark Office Re. U.S. Appl. No. 16/081,069. (7 pages).
Communication Pursuant to Article 94(3) EPC dated Jun. 2, 2021 From the European Patent Office Re. Application No. 17827121.9. (5 Pages).
European Search Report and the European Search Opinion dated Jul. 14, 2021 From the European Patent Office Re. Application No. 21170448.1. (6 Pages).
Notice of Allowance dated and Interview Summary Jul. 19, 2021 from the US Patent and Trademark Office Re. U.S. Appl. No. 16/687,726. (24 pages).
Notice of Reason(s) for Rejection dated Jun. 15, 2021 From the Japan Patent Office Re. Application No. 2020-109710 and Its Translation Into English. (12 Pages).
Notification of Office Action and Search Report dated Jul. 2, 2021 From the State Intellectual Property Office of the People's Republic of China Re. Application No. 201780055014.5. (23 Pages).
Notification of Office Action and Search Report dated Jun. 3, 2021 From the Slate Intellectual Property Office of the People's Republic of China Re. Application No. 20180014541.1 and Its Translation Into English. (17 Pages).
Notification of Office Action and Search Report dated Jul. 13, 2021 From the State Intellectual Property Office of the People's Republic of China Re. Application No. 20180781584.9 and an English Summary. (4 Pages).
Requisition by the Examiner dated Jul. 30, 2021 From the Innovation, Science and Economic Development Canada, Canadian Intellectual Property Office Re. Application No. 2,954,601. (4 Pages).
Translation Dated Jul. 22, 2021 of Notification of Office Action dated Jul. 13, 2021 From the State Intellectual Property Office of the People's Republic of China Re. Application No. 20180781584.9. (2 Pages).
Translation Dated Jul. 27, 2021 of Notification of Office Action dated Jul. 2, 2021 From the State Intellectual Property Office of the People's Republic of China Re. Application No. 201780055014.5. (12 Pages).
Notification of Office Action and Search Report dated Sep. 30, 2021 From the State Intellectual Property Office of the People's Republic of China Re. Application No. 201780073531.5 and Its Translation of Office Action Into English. (14 Pages).
Zhang "Research Progress of Interferon-Inducible Protein 10 and Its Effect in Newborn Infection Diagnosis", Chinese Journal of Neonatology. 4: 60-62, Jul. 15, 2013.
Notice of Reason(s) for Rejection dated Dec. 7, 2021 From the Japan Patent Office Re. Application No. 2020-021606 and Its Translation Into English. (11 Pages).
Final Official Action dated Nov. 29 together with Interview Summary dated Nov. 14, 2021 from US Patent and Trademark Office Re. U.S. Appl. No. 16/081,906. (45 pages).
Interview Summary dated Dec. 3, 2021 from US Patent and Trademark Office Re. U.S. Appl. No. 16/081,069. (3 pages).

Ioannidis et al. "Plasticity and Virus Specifity of the Airway Epithelial Cell Immune Response During Respiratory Virus Infection", Journal of Virology, 86(10): 5422-36, Mar. 7, 2012.
English Translation Dated Feb. 16, 2022 of Grounds of Reason of Rejection dated Jan. 27, 2022 From the Korean Intellectual Property Office Re. Application No. 10-2017-7007002. (6 Pages).
Interview Summary dated Feb. 22, 2022 from US Patent and Trademark Office Re. U.S. Appl. No. 16/081,706. (2 pages).
Notification of Office Action dated Jan. 24, 2022 From the State Intellectual Property Office of the People's Republic of China Re. Application No. 201780014568.0 and its Translation into English. (9 Pages).
Notice of Allowance dated Jan. 5, 2022 from US Patent and Trademark Office Re. U.S. Appl. No. 16/316,631. (9 pages).
Notification of Office Action dated Dec. 3, 2021 From the State Intellectual Property Office of the People's Republic of China Re. Application No. 201780055014.5 and Its Translation Into English. (5 Pages).
European Search Report and the European Search Opinion dated Oct. 6, 2021 From the European Patent Office Re. Application No. 21178885.6. (10 Pages).
Final Official Action dated Sep. 3, 2021 From the US Patent and Trademark Office Re. U.S. Appl. No. 16/316,631. (37 Pages).
Final Official Action dated Sep. 10, 2021 from the US Patent and Trademark Office Re. U.S. Appl. No. 16/081,069. (61 pages).
Notification of Office Action and Search Report dated Aug. 3, 2021 From the State Intellectual Property Office of the People's Republic of China Re. Application No. 201780055347.8 and Its Translation of Office Action Into English. (526Pages).
Notification of Office Action dated Sep. 1, 2021 From the State Intellectual Property Office of the People's Republic of China Re. Application No. 201780014568.0 and Its Translation Into English. (7 Pages).
Affymetrix "Whole-Transcript Expression Analysis", Affymetrix, 8 pages, 2007.
New England Biolabs "New England Biolabs Catalog", New England Biolabs, 1-4 pages, 1996.
Rothstein et al. "Chronic Inhibition of Superoxide Dismutase Produces Apoptotic Death of Spinal Neurons", PNAS, (10): 4155-4159, May 1994.
Zhang et al. "Expression of Tumor Necrosis Factor-Related Apoptosis-Inducing Ligand in Serum of Severe Hepatitis Patients with Nosocomial Infections and its Clinical Significance", Chinese Journal of Nosocomiology, 24, Abstract, 2012.
Requisition by the Examiner dated Nov. 5, 2021 From the Innovation, Science and Economic Development Canada, Canadian Intellectual Property Office Re. Application No. 2,968,650. (7 Pages).
Grounds of Reason of Rejection dated Jan. 27, 2022 From the Korean Intellectual Property Office Re. Application No. 10-2017-7007002. (6 Pages).
Notice of Allowance dated Feb. 7, 2022 from US Patent and Trademark Office Re. U.S. Appl. No. 16/336,528. (46 pages).
Requisition by the Examiner dated Feb. 9, 2022 From the Innovation, Science and Economic Development Canada, Canadian Intellectual Property Office Re. Application No. 2,954,601. (3 Pages).
Restriction Official Action dated Feb. 4, 2022 from US Patent and Trademark Office Re. U.S. Appl. No. 17/007,095. (6 pages).
Notice of Reason(s) for Rejection dated Dec. 14, 2021 From the Japan Patent Office Re. Application No. 2020-109710 and Its Translation Into English. (7 Pages).
Notification of Office Action and Search Repor dated Dec. 23, 2021 from the State Intellectual Property Office of the People's Republic of China Re. Application No. 201780014541.1 and Its Translation of Office Action Into English. (14 Pages).
Official Action dated Nov. 22, 2021 from the US Patent and Trademark Office Re. U.S. Appl. No. 16/998,006. (116 pages).

\* cited by examiner

FIG. 14

| Combined risk assessment | 1. Initial risk assessment based on patient's TRAIL levels | | |
|---|---|---|---|
| | Low Risk | Intermediate Risk | High Risk |
| Hypertension | Low | High | High |
| COPD | Intermediate | High | Critical |
| Diabetes | Intermediate | High | High |
| Coronary disease | Intermediate | High | Critical |

2. Patient's comorbidities

SEQUENCE LISTING

<160> NUMBER OF SEQ ID NOS: 3

<210> SEQ ID NO 1
<211> LENGTH: 281
<212> TYPE: PRT
<213> ORGANISM: Homo sapiens

<400> SEQUENCE: 1

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
```

```
                    225                 230                 235                 240
Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
                260                 265                 270

Ser Phe Phe Gly Ala Phe Leu Val Gly
                275                 280

<210> SEQ ID NO 2
<211> LENGTH: 101
<212> TYPE: PRT
<213> ORGANISM: Homo sapiens

<400> SEQUENCE: 2

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Thr Pro Arg Met Lys Arg
                85                  90                  95

Leu Trp Ala Ala Lys
            100

<210> SEQ ID NO 3
<211> LENGTH: 65
<212> TYPE: PRT
<213> ORGANISM: Homo sapiens

<400> SEQUENCE: 3

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Phe Ala Glu Asn
            35                  40                  45

Asp Cys Gln Arg Leu Met Ser Gly Gln Gln Thr Gly Ser Leu Leu Pro
    50                  55                  60

Ser
65
```

METHODS OF PROGNOSIS AND TREATMENT

FIELD AND BACKGROUND OF THE INVENTION

The present invention, in some embodiments thereof, relates to methods and prognosis of disease and treatment thereof based on the protein TNF-related apoptosis-inducing ligand (TRAIL) levels.

Disease assessment is one of the most important tasks in management of infectious disease patients. Complement to determining infection etiology, predicting patient prognosis may affect various aspects of patient management including treatment, diagnostic tests (e.g., microbiology, blood chemistry, radiology etc.), and admission. Timely identification of patients with higher chance for poor prognosis may result in more aggressive patient management procedures including for example, intensive care unit (ICU) admission, advanced therapeutics, invasive diagnostics or surgical intervention, which could reduce complications and mortality.

WO 2013/117746 teaches biomarkers including TNF-related apoptosis-inducing ligand (TRAIL) for distinguishing between a bacterial and viral infection.

Additional background art includes WO 2016/024278.

SUMMARY OF THE INVENTION

According to an aspect of some embodiments of the present invention there is provided a method of determining a management course for treating a subject having a disease, comprising measuring the TRAIL protein level in a blood sample of the subject, wherein when the TRAIL level is below a predetermined level, the subject is treated as a high-risk patient.

According to an aspect of some embodiments of the present invention there is provided a method for triaging patients comprising measuring the TRAIL protein level in a blood sample of the subject, wherein when the TRAIL level is below a predetermined level, the subject is treated as a high-risk patient.

According to an aspect of some embodiments of the present invention there is provided a method of classifying the severity of a disease of a subject comprising measuring the TRAIL protein level in a blood sample of the subject, wherein the level is indicative of the severity of the disease.

According to some embodiments of the invention, the subject is treated with a management selected from the group consisting of mechanical ventilation, invasive monitoring, last-resort drug, sedation, intensive care admission, surgical intervention and hospital admittance.

According to some embodiments of the invention, the subject is prediagnosed with the disease.

According to some embodiments of the invention, the blood sample is a fraction of whole blood.

According to some embodiments of the invention, the blood sample comprises cells selected from the group consisting of lymphocytes, monocytes and granulocytes.

According to some embodiments of the invention, the fraction is serum or plasma.

According to some embodiments of the invention, the measuring is determined electrophoretically or immunochemically.

According to some embodiments of the invention, the immunochemical determination is effected by lateral flow immunoassay, flow cytometry, radioimmunoassay, immunofluorescence or by an enzyme-linked immunosorbent assay.

According to some embodiments of the invention, the subject shows symptoms of an infectious disease.

According to some embodiments of the invention, the subject does not show symptoms of an infectious disease.

According to some embodiments of the invention, the symptoms comprise fever.

According to some embodiments of the invention, the predetermined level is below 25 pg/ml.

According to some embodiments of the invention, the predetermined level is dependent on the disease of the subject.

According to some embodiments of the invention, the method further comprises measuring the level of at least one determinant set forth in Table 2.

According to some embodiments of the invention, the at least one determinant is selected from the group consisting of IP10, PCT, IL-6 and CRP.

According to some embodiments of the invention, the level is dependent on the disease of the subject.

According to some embodiments of the invention, the subject is pre-diagnosed with the disease.

According to some embodiments of the invention, the level is below 25 pg/ml, the disease is classified as posing a high risk to the subject.

According to some embodiments of the invention, the blood sample is a fraction of whole blood.

According to some embodiments of the invention, the blood sample comprises cells selected from the group consisting of lymphocytes, monocytes and granulocytes.

According to some embodiments of the invention, the fraction is serum or plasma.

According to some embodiments of the invention, the measuring is determined electrophoretically or immunochemically.

According to some embodiments of the invention, the immunochemical determination is effected by lateral flow immunoassay, flow cytometry, radioimmunoassay, immunofluorescence or by an enzyme-linked immunosorbent assay.

According to some embodiments of the invention, the disease is an infectious disease.

According to some embodiments of the invention, the disease is a non-infectious disease.

According to some embodiments of the invention, the disease is selected from the group consisting of diabetes, chronic obstructive pulmonary disease (COPD), hypertension and a coronary disease.

According to some embodiments of the invention, the subject presents with symptoms of an infection.

According to some embodiments of the invention, the symptoms comprise fever.

According to some embodiments of the invention, the method further comprises measuring the level of at least one determinant set forth in Table 2.

According to some embodiments of the invention, the at least one determinant is selected from the group consisting of IP10, PCT, IL-6 and CRP.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 14: Exemplary algorithms for combining patient medical background conditions (e.g., comorbidities) with patient's TRAIL levels. Adding background conditions data can alter the risk level of a patient leading to improved patient management and health outcome.

DESCRIPTION OF SPECIFIC EMBODIMENTS OF THE INVENTION

The present invention, in some embodiments thereof, relates to methods and prognosis of disease and treatment thereof based on the level of protein TNF-related apoptosis-inducing ligand (TRAIL).

Figure 8:
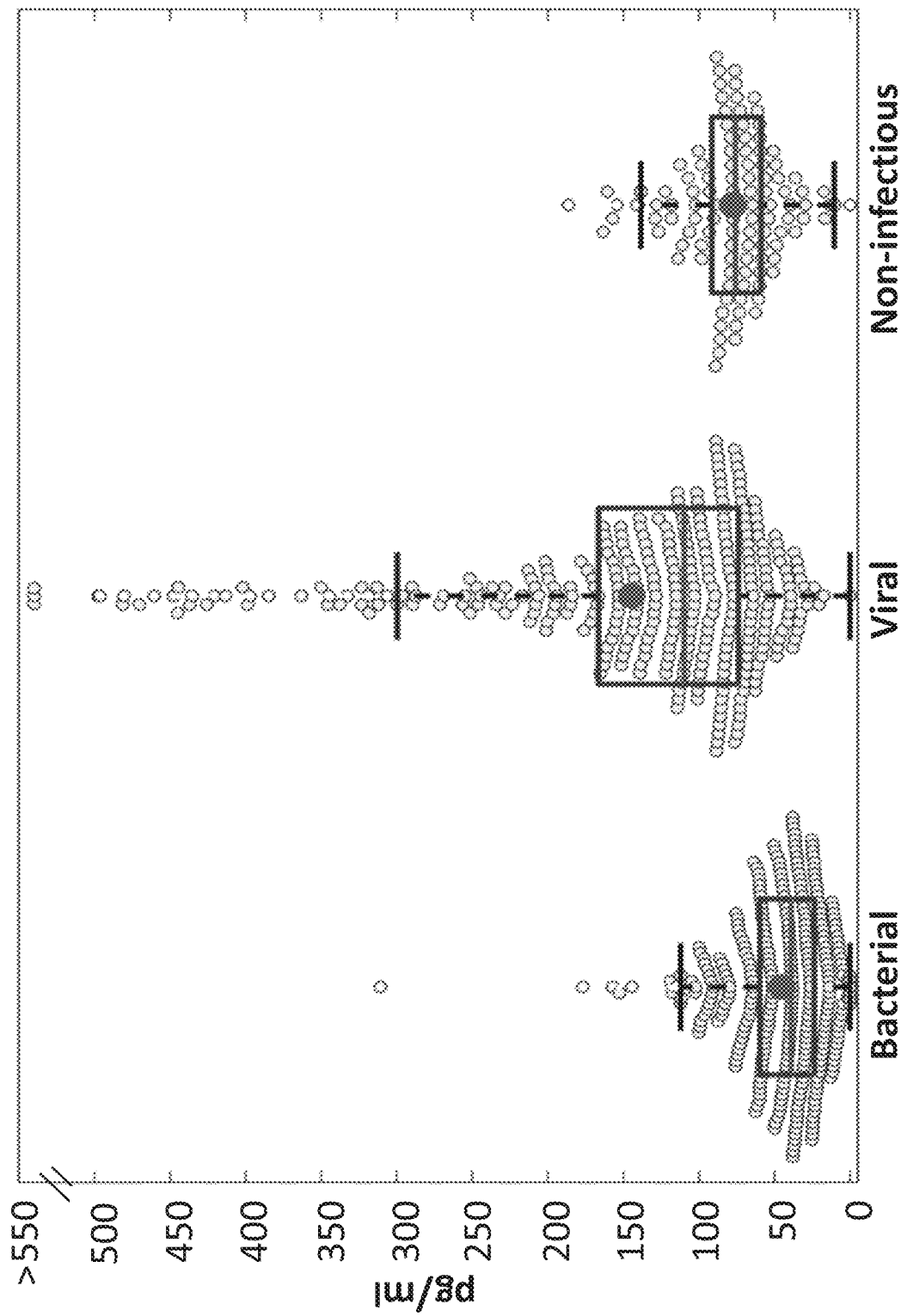
FIG. 8: Distribution of TRAIL serum levels in patients with different infection types. Box plots for TRAIL measured over the study cohort are presented. Line and circle inside the rectangle correspond to group median and average respectively; t-test p-values between bacterial and viral groups and between infectious (bacterial and viral) vs non-infectious (including healthy subjects) are depicted.
Figure 9:
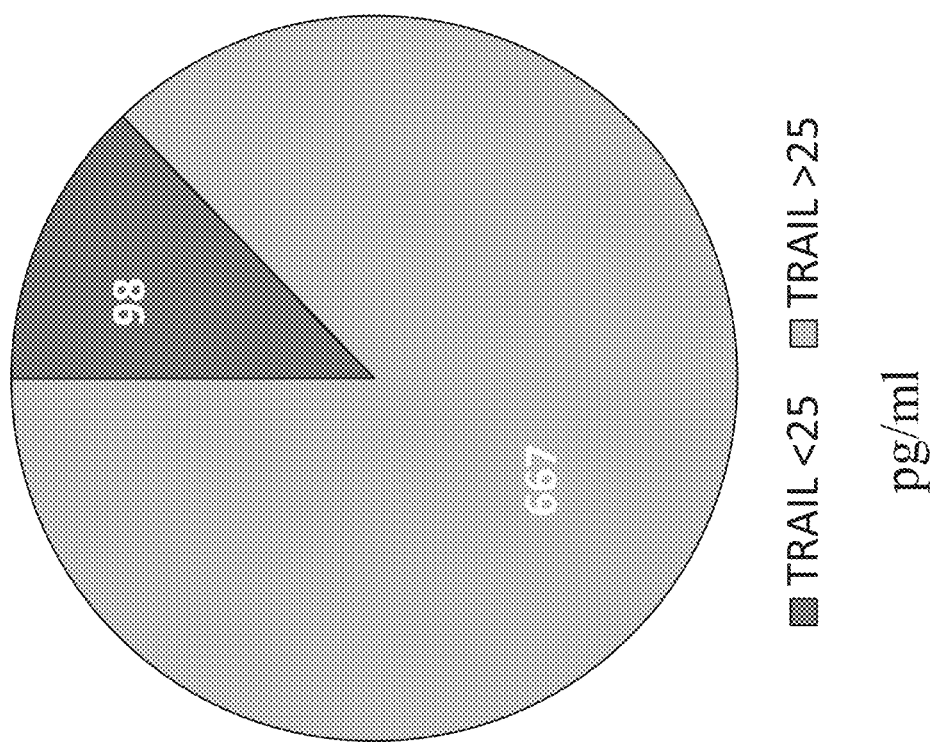
FIG. 9: Distribution of study patients according to different serum TRAIL levels.
Figure 10:
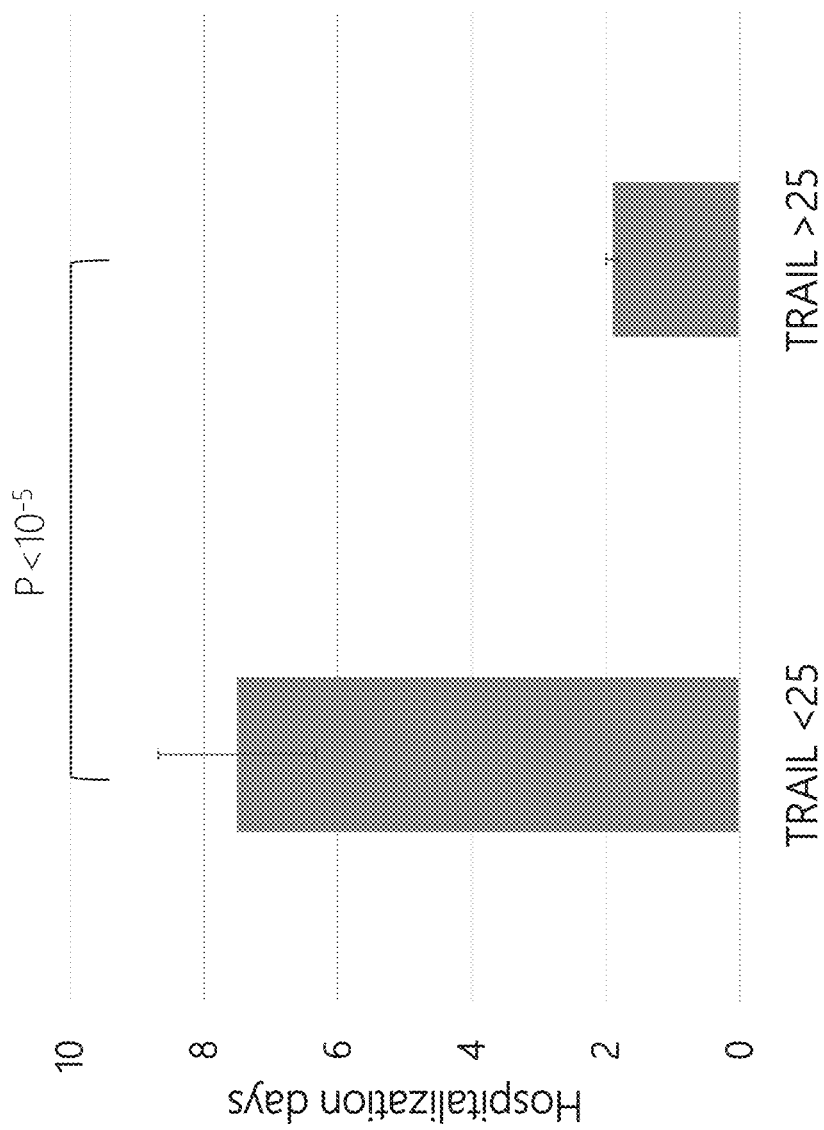
FIG. 10: Average hospitalization duration (days) in patients with different TRAIL levels.

Disease assessment is one of the most important tasks in management of infectious disease patients. As a complement to determining infection etiology, predicting patient prognosis may affect various aspects of patient management including treatment, diagnostic tests (e.g., microbiology, blood chemistry, radiology etc.), and admission. Timely identification of patients with higher chance for poor prognosis may result in more aggressive patient management procedures including for example, ICU admission, advanced therapeutics, invasive diagnostics or surgical intervention, which could reduce complications and mortality. The present inventors previously discovered that TNF-related apoptosis-inducing ligand (TRAIL) levels are decreased in bacterial patients and increased in viral patients compared to non-infectious subjects (FIG. 8). Based on their findings, they suggested TRAIL as a diagnostic marker for distinguishing between bacterial and viral patients (e.g. WO 2013/117746). Whilst reducing the present invention to practice, the present inventors have now noted that very low TRAIL levels are correlated with different aspects of disease severity and thus could be used for tailoring the correct patient management course. More specifically, the present inventors have shown that very low TRAIL levels are correlated with higher rates of ICU admission (FIGS. 11 and 12) and longer hospital length of stay (FIG. 10).

Thus, according to a first aspect of the present invention there is provided a method of determining a management course for treating a subject having a disease, comprising measuring the TRAIL protein level in a blood sample of the subject, wherein when the TRAIL level is below a predetermined level, the subject is treated as a high-risk patient.

A "subject" in the context of the present invention may be a mammal (e.g. human, dog, cat, horse, cow, sheep, pig or goat). According to another embodiment, the subject is a bird (e.g. chicken, turkey, duck or goose). According to a particular embodiment, the subject is a human. The subject may be male or female. The subject may be an adult (e.g. older than 18, 21, or 22 years or a child (e.g. younger than 18, 21 or 22 years). In another embodiment, the subject is an adolescent (between 12 and 21 years), an infant (29 days to less than 2 years of age) or a neonate (birth through the first 28 days of life).

In one embodiment, the subject of this aspect of the present invention is afflicted with the disease, yet does not necessarily show symptoms of the disease—e.g. the disease may be managed using known therapeutics. For example, the subject may be a diabetic subject, yet his glucose levels may be normal since he is taking anti-hyperglycemic medication. Preferably the subject of this aspect of the present invention has already been diagnosed with the disease.

In another embodiment, the subjects of this aspect of the present invention present with symptoms of a disease.

Exemplary symptoms of a disease include but are not limited to abnormal blood pressure, abnormal heart rate, abnormal red blood count, abnormal white blood count, abnormal body temperature, abnormal respiratory rate, abnormal lucidity or alertness.

In one embodiment the symptoms which the subject may present with are symptoms of an infectious disease. Exemplary symptoms include but are not limited to fever, nausea, headache, sore throat, runny nose, rash and/or muscle soreness.

In another embodiment the symptoms which the subject may present with are symptoms of a cardiac disease (e.g. chest pain, high blood pressure). The subject of this embodiment, may further present with symptoms of an infectious disease (e.g. fever).

In still another embodiment, the symptoms which the subject may present with are symptoms of a pulmonary disease (e.g. cough, breathing difficulty). The subject of this embodiment may further present with symptoms of an infectious disease (e.g. fever).

In still another embodiment, the symptoms which the subject may present with are symptoms of a metabolic disease (e.g. high blood sugar). The subject of this embodiment, may further present with symptoms of an infectious disease (e.g. fever).

It will be appreciated that when the TRAIL level is below a predetermined amount, e.g. below 30 pg/ml (or any of the levels described herein), this information may also be used to classify a pre-diagnosed disease to be of higher severity than if the TRAIL levels were above a predetermined amount. Conversely, when the TRAIL level is above a predetermined amount, e.g. above 30 pg/ml (or any of the levels described herein), this information may also be used to classify a pre-diagnosed disease to be of lower severity than if the TRAIL levels were below a predetermined amount.

The predetermined level in some embodiments of the present invention (also referred to herein as "highly sensitive TRAIL) is the level of TRAIL which classifies disease severity and not necessarily disease type (e.g. bacterial vs. viral).

It will be appreciated that the threshold level below which the risk to the patient (or the prognosis of the disease) is raised may depend on the disease from which the patient is suffering.

Thus, for example, for a healthy patient, a serum protein TRAIL level below 30 pg/ml may indicate high risk, whereas for a patient with a disease (e.g. COPD), a serum protein TRAIL which indicates high risk is higher—e.g. 40 pg/ml. Thus, one can use a comorbidity dependent normalization or stratification scheme to adjust for background condition related differences. Performing comorbidity dependent normalization, stratification or distinct mathematical formulas can be used to improve the accuracy of TRAIL for differentiating between different types of infections or for predicting disease severity and health outcome.

For example, one skilled in the art can generate a function that fits the population mean levels of TRAIL as function of comorbidity and use it to normalize the TRAIL levels of individual subjects across different background conditions. Another example is to stratify subjects according to their background conditions and determine condition specific thresholds or index values for each group independently.

Thus, according to another aspect of the present invention there is provided a method of classifying the severity of a disease of a subject comprising measuring the TRAIL protein level in a blood sample of the subject, wherein the level is indicative of the severity of the disease.

The pre-diagnosed disease may be an infectious disease or a non-infectious disease. For example if a diabetic patient has a serum TRAIL level of below 30 pg/ml (or any of the levels described herein), the diabetes can be classified as severe and warrant additional treatment that would otherwise not have been prescribed had the TRAIL levels been above the predetermined level.

As another example, if a hypertensive patient has as serum TRAIL level of below 30 pg/ml (or any of the levels described herein), the hypertension can be classified as severe and warrant additional treatment that would otherwise not have been prescribed had the TRAIL levels been above the predetermined level. Other diseases or disorders for which severity status can be classified include but are not limited to bacterial infections (e.g. bacteremia, meningitis, respiratory tract infections, urinal tract infections etc.), COPD, chronic lung disease, diabetes, hypertension, sepsis, physical injury and trauma, cardiovascular diseases, multi-organ failure associated diseases, drug-induced nephrotoxicity, acute kidney disease, renal injury, kidney failure, advanced cirrhosis and liver failure, acute or chronic left heart failure, pulmonary hypertension with/without right heart failure, and various types of malignancies.

Thus, the inventors further provide a recommended algorithm for combining initial risk assessment based on the patient TRAIL levels with known comorbidities of the patient (see FIG. 14). For example, TRAIL levels indicative of a viral infection could result in categorizing the patient as a low risk patient. However, adding information about relevant background disease such as COPD will lead to re-classifying the patient as an intermediate risk patient.

For any of the aspects disclosed herein, the term "measuring" or "measurement," or alternatively "detecting" or "detection," means assessing the presence, absence, quantity or amount (which can be an effective amount) of the determinant within a clinical or subject-derived sample, including the derivation of qualitative or quantitative concentration levels of such determinants.

A "sample" in the context of the present invention is a biological sample isolated from a subject and can include, by way of example and not limitation, whole blood, serum, plasma, saliva, mucus, breath, urine, CSF, sputum, sweat, stool, hair, seminal fluid, biopsy, rhinorrhea, tissue biopsy, cytological sample, platelets, reticulocytes, leukocytes, epithelial cells, or whole blood cells.

In a particular embodiment, the sample is a blood sample—e.g. serum, plasma, whole blood. The sample may be a venous sample, peripheral blood mononuclear cell sample or a peripheral blood sample. Preferably, the sample comprises white blood cells including for example granulocytes, lymphocytes and/or monocytes. In one embodiment, the sample is depleted of red blood cells.

The sample is preferably derived from the subject no more than 72 hours, no more than 60 hours, no more than 48 hours, no more than 36 hours, no more than one 24 hours or even no more than 12 hours following symptom onset.

The sample may be fresh or frozen.

According to a particular embodiment, the subject does not show signs of having had a heart attack (e.g. has a normal level of creatine kinase, troponin or serum myoglobin, and/or has a normal ECG or EKG).

According to yet another embodiment, the subject does not have cancer.

TRAIL: The protein encoded by this gene is a cytokine that belongs to the tumor necrosis factor (TNF) ligand family. The present invention contemplates measuring either the soluble and/or the membrane form of this protein. In one embodiment, only the soluble form of this protein is measured. Additional names of the gene include without limitations APO2L, TNF-related apoptosis-inducing ligand, TNFSF10 and CD253. This protein binds to several members of the TNF receptor superfamily such as TNFRSF10A/TRAILR1, TNFRSF10B/TRAILR2, TNFRSF10C/TRAILR3, TNFRSF10D/TRAILR4, and possibly also to TNFRSF11B/OPG.

Additional information concerning TRAIL is provided in Table 1, herein below.

TABLE 1

| Protein symbol | Full Gene Name | RefSeq DNA sequence | RefSeq proteins |
|---|---|---|---|
| TRAIL | Tumor necrosis factor superfamily member 10 | NC_000003.12 NC_018914.2 NT_005612.17 | NP_001177871.1 NP_001177872.1 NP_003801.1 |

Exemplary amino acid sequences of TRAIL are set forth as in SEQ ID NOS: 1-3.

Methods of measuring the level of TRAIL polypeptide are well known in the art and include, e.g., immunoassays based on antibodies to proteins, aptamers or molecular imprints.

TRAIL can be detected in any suitable manner, but are typically detected by contacting a sample from the subject with an antibody, which binds the TRAIL and then detecting the presence or absence of a reaction product. The antibody may be monoclonal, polyclonal, chimeric, or a fragment of the foregoing, and the step of detecting the reaction product may be carried out with any suitable immunoassay.

In one embodiment, the antibody which specifically binds the determinant is attached (either directly or indirectly) to a signal producing label, including but not limited to a radioactive label, an enzymatic label, a hapten, a reporter dye or a fluorescent label.

Immunoassays carried out in accordance with some embodiments of the present invention may be homogeneous assays or heterogeneous assays. In a homogeneous assay the immunological reaction usually involves the specific antibody (e.g., anti-determinant antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels, which may be employed, include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase.

The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al., titled "Methods for Modulating Ligand-Receptor Interactions and their Application," U.S. Pat. No. 4,659,678 to Forrest et al., titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label." The determinant can also be detected with antibodies using flow cytometry. Those skilled in the art will be familiar with flow cytometric techniques which may be useful in carrying out the methods disclosed herein (Shapiro 2005). These include, without limitation, Cytokine Bead Array (Becton Dickinson) and Luminex technology.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques.

In particular embodiments, the antibodies of the present invention are monoclonal antibodies.

Suitable sources for antibodies for the detection of determinants include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptide determinants described herein.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Those skilled in the art will be familiar with numerous suitable detectors that widely available from a variety of commercial sources and may be useful for carrying out the method disclosed herein. Commonly, an optical image of a substrate comprising bound labeling moieties is digitized for subsequent computer analysis. See generally The Immunoassay Handbook [The Immunoassay Handbook. Third Edition. 2005].

Examples of "Monoclonal antibodies for measuring TRAIL", include without limitation: Mouse, Monoclonal (55B709-3) IgG; Mouse, Monoclonal (2E5) IgG1; Mouse, Monoclonal (2E05) IgG1; Mouse, Monoclonal (M912292) IgG1 kappa; Mouse, Monoclonal (IIIF6) IgG2b; Mouse, Monoclonal (2E1-1B9) IgG1; Mouse, Monoclonal (RIK-2) IgG1, kappa; Mouse, Monoclonal M181 IgG1; Mouse, Monoclonal VI10E IgG2b; Mouse, Monoclonal MAB375 IgG1; Mouse, Monoclonal MAB687 IgG1; Mouse, Monoclonal HS501 IgG1; Mouse, Monoclonal clone 75411.11 Mouse IgG1; Mouse, Monoclonal T8175-50 IgG; Mouse, Monoclonal 2B2.108 IgG1; Mouse, Monoclonal B-T24 IgG1; Mouse, Monoclonal 55B709.3 IgG1; Mouse, Monoclonal D3 IgG1; Goat, Monoclonal C19 IgG; Rabbit, Monoclonal H257 IgG; Mouse, Monoclonal 500-M49 IgG; Mouse, Monoclonal 05-607 IgG; Mouse, Monoclonal B-T24 IgG1; Rat, Monoclonal (N2B2), IgG2a, kappa; Mouse, Monoclonal (1A7-2B7), IgG1; Mouse, Monoclonal (55B709.3), IgG and Mouse, Monoclonal B-S23*IgG1.

Soluble TRAIL and membrane TRAIL can be distinguished by using different measuring techniques and samples. For example, Soluble TRAL can be measured without limitation in cell free samples such as serum or plasma, using without limitation lateral flow immunoassay (LFIA), as further described herein below. Membrane TRAIL can be measured in samples that contain cells using cell based assays including without limitation flow cytometry, ELISA, and other immunoassays.

Lateral Flow Immunoassays (LFIA):

This is a technology which allows rapid measurement of analytes at the point of care (POC) and its underlying principles are described below. According to one embodiment, LFIA is used in the context of a hand-held device.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex.

After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick, that simply acts as a waste container. Lateral Flow Tests can operate as either competitive or sandwich assays.

Different formats may be adopted in LFIA. Strips used for LFIA contain four main components. A brief description of each is given before describing format types.

Sample application pad: It is made of cellulose and/or glass fiber and sample is applied on this pad to start assay. Its function is to transport the sample to other components of lateral flow test strip (LFTS). Sample pad should be capable of transportation of the sample in a smooth, continuous and homogenous manner. Sample application pads are sometimes designed to pretreat the sample before its transportation. This pretreatment may include separation of sample components, removal of interferences, adjustment of pH, etc.

Conjugate pad: It is the place where labeled biorecognition molecules are dispensed. Material of conjugate pad should immediately release labeled conjugate upon contact with moving liquid sample. Labeled conjugate should stay stable over entire life span of lateral flow strip. Any variations in dispensing, drying or release of conjugate can change results of assay significantly. Poor preparation of labeled conjugate can adversely affect sensitivity of assay. Glass fiber, cellulose, polyesters and some other materials are used to make conjugate pad for LFIA. Nature of conjugate pad material has an effect on release of labeled conjugate and sensitivity of assay.

Nitrocellulose membrane: It is highly critical in determining sensitivity of LFIA. Nitrocellulose membranes are available in different grades. Test and control lines are drawn over this piece of membrane. So an ideal membrane should provide support and good binding to capture probes (antibodies, aptamers etc.). Nonspecific adsorption over test and control lines may affect results of assay significantly, thus a good membrane will be characterized by lesser non-specific adsorption in the regions of test and control lines. Wicking rate of nitrocellulose membrane can influence assay sensitivity. These membranes are easy to use, inexpensive, and offer high affinity for proteins and other biomolecules. Proper dispensing of bioreagents, drying and blocking play a role in improving sensitivity of assay.

Adsorbent pad: It works as sink at the end of the strip. It also helps in maintaining flow rate of the liquid over the membrane and stops back flow of the sample. Adsorbent capacity to hold liquid can play an important role in results of assay.

All these components are fixed or mounted over a backing card. Materials for backing card are highly flexible because they have nothing to do with LFIA except providing a platform for proper assembling of all the components. Thus backing card serves as a support and it makes easy to handle the strip.

Major steps in LFIA are (i) preparation of antibody against target analyte (ii) preparation of label (iii) labeling of biorecognition molecules (iv) assembling of all components onto a backing card after dispensing of reagents at their proper pads (v) application of sample and obtaining results.

Sandwich format: In a typical format, label (Enzymes or nanoparticles or fluorescence dyes) coated antibody or aptamer is immobilized at conjugate pad. This is a temporary adsorption which can be flushed away by flow of any buffer solution. A primary antibody or aptamer against target analyte is immobilized over test line. A secondary antibody or probe against labeled conjugate antibody/aptamer is immobilized at control zone.

Sample containing the analyte is applied to the sample application pad and it subsequently migrates to the other parts of strip. At conjugate pad, target analyte is captured by the immobilized labeled antibody or aptamer conjugate and results in the formation of labeled antibody conjugate/analyte complex. This complex now reaches at nitrocellulose membrane and moves under capillary action. At test line, label antibody conjugate/analyte complex is captured by another antibody which is primary to the analyte. Analyte becomes sandwiched between labeled and primary antibodies forming labeled antibody conjugate/analyte/primary antibody complex. Excess labeled antibody conjugate will be captured at control zone by secondary antibody. Buffer or excess solution goes to absorption pad. Intensity of color at test line corresponds to the amount of target analyte and is measured with an optical strip reader or visually inspected. Appearance of color at control line ensures that a strip is functioning properly.

Competitive format: Such a format suits best for low molecular weight compounds which cannot bind two antibodies simultaneously. Absence of color at test line is an indication for the presence of analyte while appearance of color both at test and control lines indicates a negative result. Competitive format has two layouts. In the first layout, solution containing target analyte is applied onto the sample application pad and prefixed labeled biomolecule (antibody/aptamer) conjugate gets hydrated and starts flowing with moving liquid. Test line contains pre-immobilized antigen (same analyte to be detected) which binds specifically to label conjugate. Control line contains pre-immobilized secondary antibody which has the ability to bind with labeled antibody conjugate. When liquid sample reaches at the test line, pre-immobilized antigen will bind to the labeled conjugate in case target analyte in sample solution is absent or present in such a low quantity that some sites of labeled antibody conjugate were vacant. Antigen in the sample solution and the one which is immobilized at test line of strip compete to bind with labeled conjugate. In another layout, labeled analyte conjugate is dispensed at conjugate pad while a primary antibody to analyte is dispensed at test line. After application of analyte solution a competition takes place between analyte and labeled analyte to bind with primary antibody at test line.

Multiplex detection format: Multiplex detection format is used for detection of more than one target species and assay is performed over the strip containing test lines equal to number of target species to be analyzed. It is highly desirable to analyze multiple analytes simultaneously under same set of conditions. Multiplex detection format is very useful in clinical diagnosis where multiple analytes which are interdependent in deciding about the stage of a disease are to be detected. Lateral flow strips for this purpose can be built in various ways i.e. by increasing length and test lines on conventional strip, making other structures like stars or T-shapes. Shape of strip for LFIA will be dictated by number of target analytes. Miniaturized versions of LFIA based on microarrays for multiplex detection of DNA sequences have been reported to have several advantages such as less consumption of test reagents, requirement of lesser sample volume and better sensitivity.

Labels: Any material that is used as a label should be detectable at very low concentrations and it should retain its properties upon conjugation with biorecognition molecules. This conjugation is also expected not to change features of biorecognition probes. Ease in conjugation with biomolecules and stability over longer period of time are desirable features for a good label. Concentrations of labels down to $10^{-9}$ M are optically detectable. After the completion of assay, some labels generate direct signal (as color from gold colloidal) while others require additional steps to produce analytical signal (as enzymes produce detectable product upon reaction with suitable substrate). Hence the labels which give direct signal are preferable in LFA because of less time consumption and reduced procedure.

Gold nanoparticles: Colloidal gold nanoparticles are the most commonly used labels in LFA. Colloidal gold is inert and gives very perfect spherical particles. These particles have very high affinity toward biomolecules and can be easily functionalized. Optical properties of gold nanoparticles are dependent on size and shape. Size of particles can be tuned by use of suitable chemical additives. Their unique features include environment friendly preparation, high affinity toward proteins and biomolecules, enhanced stability, exceptionally higher values for charge transfer and good optical signaling. Optical signal of gold nanoparticles in colorimetric LFA can be amplified by deposition of silver, gold nanoparticles and enzymes.

Magnetic particles and aggregates: Colored magnetic particles produce color at the test line which is measured by an optical strip reader but magnetic signals coming from magnetic particles can also be used as detection signals and recorded by a magnetic assay reader. Magnetic signals are stable for longer time compared to optical signals and they enhance sensitivity of LFA by 10 to 1000 folds.

Fluorescent and luminescent materials: Fluorescent molecules are widely used in LFA as labels and the amount of fluorescence is used to quantitate the concentration of analyte in the sample. Detection of proteins is accomplished by using organic fluorophores such as rhodamine as labels in LFA.

Current developments in nanomaterial have headed to manufacture of quantum dots which display very unique electrical and optical properties. These semiconducting particles are not only water soluble but can also be easily combined with biomolecules because of closeness in dimensions. Owing to their unique optical properties, quantum dots have come up as a substitute to organic fluorescent dyes Like gold nanoparticles QDs show size dependent optical properties and a broad spectrum of wavelengths can be monitored. Single light source is sufficient to excite quantum dots of all different sizes. QDs have high photo stability and absorption coefficients.

Upconverting phosphors (UCP) are characterized by their excitation in infra-red region and emission in high energy visible region. Compared to other fluorescent materials, they have a unique advantage of not showing any auto fluorescence. Because of their excitation in IR regions, they do not photo degrade biomolecules. A major advantage lies in their production from easily available bulk materials. Although difference in batch to batch preparation of UCP reporters can affect sensitivity of analysis in LFA, it was observed that they can enhance sensitivity of analytical signal by 10 to 100 folds compared to gold nanoparticles or colored latex beads, when analysis is carried out under same set of biological conditions.

Enzymes: Enzymes are also employed as labels in LFA. But they increase one step in LFA which is application of suitable substrate after complete assay. This substrate will produce color at test and control lines as a result of enzymatic reaction. In case of enzymes, selection of suitable enzyme substrate combination is one necessary requirement in order to get a colored product for strip reader or electroactive product for electrochemical detection. In other words, sensitivity of detection is dependent on enzyme substrate combination.

Colloidal carbon: Colloidal carbon is comparatively inexpensive label and its production can be easily scaled up. Because of their black color, carbon NPs can be easily detected with high sensitivity. Colloidal carbon can be functionalized with a large variety of biomolecules for detection of low and high molecular weight analytes.

Detection systems: In case of gold nanoparticles or other color producing labels, qualitative or semi-quantitative analysis can be done by visual inspection of colors at test and control lines. The major advantage of visual inspection is rapid qualitative answer in "Yes" or "NO". Such quick replies about presence of an analyte in clinical analysis have very high importance. Such tests help doctors to make an immediate decision near the patients in hospitals in situations where test results from central labs cannot be waited for because of huge time consumption. But for quantification, optical strip readers are employed for measurement of the intensity of colors produced at test and control lines of strip. This is achieved by inserting the strips into a strip reader and intensities are recorded simultaneously by imaging softwares. Optical images of the strips can also be recorded with a camera and then processed by using a suitable software. Procedure includes proper placement of strip under the camera and a controlled amount of light is thrown on the areas to be observed. Such systems use monochromatic light and wavelength of light can be adjusted to get a good contrast among test and control lines and background. In order to provide good quantitative and reproducible results, detection system should be sensitive to different intensities of colors. Optical standards can be used to calibrate an optical reader device. Automated systems have advantages over manual imaging and processing in terms of time consumption, interpretation of results and adjustment of variables.

In case of fluorescent labels, a fluorescence strip reader is used to record fluorescence intensity of test and control lines. Fluorescence brightness of test line increased with an increase in nitrated seruloplasmin concentration in human serum when it was detected with a fluorescence strip reader. A photoelectric sensor was also used for detection in LFIA where colloidal gold is exposed to light emitting diode and resulting photoelectrons are recorded. Chemiluminescence which results from reaction of enzyme and substrate is measured as a response to amount of target analyte. Magnetic strip readers and electrochemical detectors are also reported as detection systems in LFTS but they are not very common. Selection of detector is mainly determined by the label employed in analysis.

As mentioned above, when the TRAIL protein serum level is lower than a predetermined level, the subject is classified as a high-risk patient. The predetermined level may be below 30 pg/ml, below 25 pg/ml, below 20 pg/ml, below 15 pg/ml or even below 10 pg/ml.

The term "risk assessment" refers to as assignment of a probability to experience certain adverse events (e.g. death, hospitalization or admission to ICU) to an individual. Hereby, the individual may preferably be accounted to a certain risk category, wherein categories comprise for instance high risk versus low risk, or risk categories based on numeral values, such as risk category 1, 2, 3, etc. 2.

According to a specific embodiment, the TRAIL protein level is used to stratify the subject into one of four levels—low, intermediate, high and critical.

In one embodiment, the risk assessment is made in the emergency department of a hospital.

Emergency departments (ED) are progressively overwhelmed by patients with both urgent and non-urgent problems. This leads to overfilled ED waiting rooms with long waiting times, detrimental outcomes and unsatisfied patients. As a result, patients needing urgent care may not be treated in time, whereas patients with non-urgent problems may unnecessarily receive expensive and dispensable treatments. Time to effective treatment is among the key predictors for outcomes across different medical conditions, including patients with septicaemia, pneumonia, stroke and myocardial infarction. For these reasons, the present inventors propose use of the presently disclosed risk stratification system in the ED is essential for an optimal initial triage of medical patients.

In another embodiment, the risk assessment is made in the intensive care unit of a hospital.

The risk measurement may be used to determine a management course for the patient. The risk measurement may aid in selection of treatment priority and also site-of-care decisions (i.e. outpatient vs. inpatient management) and early identification and organization of post-acute care needs.

When a patient has been assessed as being at high risk, the management course is typically more aggressive than if he had not been assessed as being at high risk. Thus, treatment options such as mechanical ventilation, life support, catheterization, hemofiltration, invasive monitoring, sedation, intensive care admission, surgical intervention, drug of last resort and hospital admittance may be selected which may otherwise not have been considered the preferred method of treatment if the patient had not been assessed as being at high risk.

Classification of subjects into subgroups according to this aspect of the present invention is preferably done with an acceptable level of clinical or diagnostic accuracy. An "acceptable degree of diagnostic accuracy", is herein defined as a test or assay (such as the test used in some aspects of the invention) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict risk with at least 75% total accuracy, more preferably 80%, 85%, 90%, 95%, 97%, 98%, 99% or greater total accuracy. Alternatively, the methods predict the correct management or treatment with an MCC larger than 0.2, 0.3, 0.4, 0.5, 0.6, 0.7, 0.8, 0.9 or 1.0.

On the basis of the level of TRAIL, the practitioner may determine a more severe treatment course than for a subject who represents with the same symptoms yet has a TRAIL protein serum level above the predetermined level.

Thus, for example when the TRAIL level is below the predetermined amount, the practitioner may predict or recommend intensive care unit (ICU) admission.

According to another embodiment of the present invention, when the TRAIL level is below the predetermined amount, patient mortality is predicted within 1, 2, 3, 5, 7, 10, 15, or 20 days after TRAIL measurement.

According to another embodiment of the present invention, the TRAIL is used for predicting or recommending a prolonged hospital length of stay.

In yet another embodiment, when the TRAIL level is below the predetermined amount, patient re-admission is predicted or recommended.

In yet another embodiment, when the TRAIL level is below the predetermined amount, invasive monitoring is recommended.

In yet another embodiment, when the TRAIL level is below the predetermined amount, mechanical ventilation is recommended.

In yet another embodiment, when the TRAIL level is below the predetermined amount, last-resort drug administration is recommended.

Such agents for example may be for example experimental agents that have not been given full FDA approval. Other last resort agents are those that are known to be associated with severe side effects. Another exemplary last resort agent is an antibiotic such as vancomycin (which is typically not provided so as to prevent the spread of antibiotic resistance). Another exemplary last resort agent is a broad spectrum antibiotic.

It will be appreciated that agents that are not typically considered as last resort agents can also be provided, but in doses which exceed the clinically acceptable dose.

According to this aspect of the present invention, if the TRAIL level is above a predetermined level, then the patient should typically not be treated with a last resort agent.

In yet another embodiment, when the TRAIL level is below the predetermined amount, sedation is recommended.

In yet another embodiment, when the TRAIL level is below the predetermined amount, surgical intervention is recommended.

Following predictions described herein based on TRAIL levels, hospital resources may be reallocated or hospital management may be altered.

For example, in one embodiment, the TRAIL level is used in triage in the emergency room and on the basis of a TRAIL being below a predetermined level, a patient might be seen/attended to prior to a patient who has a TRAIL level above a predetermined level.

It will be appreciated that the TRAIL level may be used in conjunction with other markers/tests etc. in order to determine a management course and/or to assess risk to subject.

Exemplary markers include for example those disclosed in Table 2 herein below.

TABLE 2

| Protein symbol | Full Gene Name | RefSeq DNA sequence | RefSeq proteins |
| --- | --- | --- | --- |
| CRP | C-reactive protein, pentraxin-related | NC_000001.11 NT_004487.20 NC_018912.2 | NP_000558.2 |
| IP-10 | Chemokine (C—X—C motif) ligand 10 | NC_000004.12 NC_018915.2 NT_016354.20 | NP_001556.2 |
| IL1R/IL1R1/ IL1RA | Interleukin 1 receptor, type I | NC_000002.12 NT_005403.18 NC_018913.2 | NP_000868.1 NP_001275635.1 |
| SAA/SAA1 | Serum amyloid A1 | NC_000011.10 NC_018922.2 NT_009237.19 | NP_000322.2 NP_001171477.1 NP_954630.1 |
| TREM1 | Triggering receptor expressed on myeloid cells 1 | NC_000006.12 NT_007592.16 NC_018917.2 | NP_001229518.1 NP_001229519.1 NP_061113.1 |
| TREM2 | Triggering receptor expressed on myeloid cells 2 | NC_000006.12 NT_007592.16 NC_018917.2 | NP_001258750.1 NP_061838.1 |
| RSAD2 | Radical S-adenosyl methionine domain containing 2 | NC_000002.12 NT_005334.17 NC_018913.2 | NP_542388.2 |
| NGAL | Lipocalin 2 | NC_000009.12 NC_018920.2 NT_008470.20 | NP_005555.2 |
| MMP8 | Matrix metallopeptidase 8 | NC_000011.10 NT_033899.9 NC_018922.2 | NP_001291370.1 NP_001291371.1 NP_002415.1 |

TABLE 2-continued

| Protein symbol | Full Gene Name | RefSeq DNA sequence | RefSeq proteins |
| --- | --- | --- | --- |
| MX1 | MX Dynamin-Like GTPase 1 | NC_000021.9 NT_011512.12 NC_018932.2 | NP_001138397.1 NP_001171517.1 NP_001269849.1 NP_002453.2 |
| Procalcitonin (PCT) | Calcitonin-related polypeptide alpha | NC_000011.10 NC_018922.2 NT_009237.19 | NP_001029124.1 NP_001029125.1 NP_001732.1 |
| IL-6 | Interleukin 6 | NC_000007.14 NT_007819.18 NC_018918.2 | NP_000591.1 |
| Neopterin | 2-amino-6-(1,2,3-trihydroxypropyl)-1H-pteridin-4-one IUPAC name | N/A | N/A |

Furthermore, traditional risk factors and additional clinical parameters may be used to classify the severity of the disease.

"Traditional laboratory risk factors" encompass biomarkers isolated or derived from subject samples and which are currently evaluated in the clinical laboratory and used in traditional global risk assessment algorithms, such as absolute neutrophil count (abbreviated ANC), absolute lymphocyte count (abbreviated ALC), white blood count (abbreviated WBC), neutrophil % (defined as the fraction of white blood cells that are neutrophils and abbreviated Neu (%)), lymphocyte % (defined as the fraction of white blood cells that are lymphocytes and abbreviated Lym (%)), monocyte % (defined as the fraction of white blood cells that are monocytes and abbreviated Mon (%)), Sodium (abbreviated Na), Potassium (abbreviated K), Bilirubin (abbreviated Bili).

"Clinical parameters" encompass all non-sample or non-analyte biomarkers of subject health status or other characteristics, such as, without limitation, age (Age), ethnicity (RACE), gender (Sex), core body temperature (abbreviated "temperature"), maximal core body temperature since initial appearance of symptoms (abbreviated "maximal temperature"), time from initial appearance of symptoms (abbreviated "time from symptoms") or family history (abbreviated FamHX).

Exemplary combinations of markers which may be used for risk management include, but are not limited to: TRAIL+CRP; TRAIL+PCT; TRAIL+IL-6; TRAIL+IP-10; TRAIL+NGAL; TRAIL+CRP+PCT; TRAIL+CRP+NGAL; TRAIL+CRP+IP-10; TRAIL+CRP+IL-6; TRAIL+PCT+IL-6; TRAIL+PCT+IP-10; TRAIL+PCT+NGAL; TRAIL+CRP+IL-6+PCT; TRAIL+CRP+IL-6+NGAL; TRAIL+CRP+IL-6+IP-10; TRAIL+NGAL+IL-6+PCT; TRAIL+IP-10+IL-6+PCT; TRAIL+WBC; TRAIL+ANC; TRAIL+temperature; TRAIL+mean arterial pressure; TRAIL+pH arterial; TRAIL+heart rate; TRAIL+respiratory rate; TRAIL+AaDO2 or PaO2; TRAIL+sodium; TRAIL+potassium; TRAIL+creatinine; TRAIL+hematocrit.

Combining the levels of TRAIL and the other marker is typically effected using algorithms or formulas as described herein below.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value". Non-limiting examples of "formulas" include sums, ratios, and regression operators, such as coefficients or exponents, biomarker value transformations and normalizations (including, without limitation, those normalization schemes based on clinical-determinants, such as gender, age, or ethnicity), rules and guidelines, statistical classification models, and neural networks trained on historical populations.

Of particular use in combining determinants are linear and non-linear equations and statistical classification analyses to determine the relationship between levels of determinants detected in a subject sample and the subject's risk assessment. In panel and combination construction, of particular interest are structural and syntactic statistical classification algorithms, and methods of index construction, utilizing pattern recognition features, including established techniques such as cross-correlation, Principal Components Analysis (PCA), factor rotation, Logistic Regression (Log Reg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, and Hidden Markov Models, among others. Other techniques may be used in survival and time to event hazard analysis, including Cox, Weibull, Kaplan-Meier and Greenwood models well known to those of skill in the art. Many of these techniques are useful either combined with a determinant selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV).

Any formula may be used to combine TRAIL levels with the additional determinant into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of infection. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual determinant measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on clinical-determinants such as age, time from symptoms, gender, race, or sex, where specific formula are used solely on subjects within a class or continuously combining a clinical-determinants as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al, (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula.

Some determinants may exhibit trends that depends on the patient age (e.g. the population baseline may rise or fall as a function of age). One can use an 'Age dependent normalization or stratification' scheme to adjust for age related differences. Performing age dependent normalization or stratification can be used to improve the accuracy of determinants for differentiating between different types of infections. For example, one skilled in the art can generate a function that fits the population mean levels of each determinant as function of age and use it to normalize the determinant of individual subjects levels across different ages. Another example is to stratify subjects according to their age and determine age specific thresholds or index values for each age group independently.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In the context of the present invention, the following abbreviations may be used: ANC=Absolute neutrophil count; ANN=Artificial neural networks; AUC=Area under the receiver operating curve; BP=*Bordetella pertussis*; CHF=Congestive heart failure; CI=Confidence interval; CID=Congenital immune deficiency; CLL=Chronic lymphocytic leukemia; CMV=Cytomegalovirus; CNS=Central nervous system; COPD=Chronic obstructive pulmonary disease; CP=*Chlamydophila* pneumonia; CRP=C-reactive protein; CSF=Cerebrospinal fluid; CV=Coefficient of variation; DOR=Diagnostic odds ratio; EBV=Epstein bar virus; eCRF=Electronic case report form; ED=Emergency department, ELISA=Enzyme-linked immunosorbent assay; FDR=False discovery rate; FMF=Familial Mediterranean fever; G-CSF=Granulocyte colony-stimulating factor; GM-CSF=Granulocyte-macrophage colony-stimulating factor; HBV=Hepatitis B virus; HCV=Hepatitis C virus; HI=*Haemophilus* influenza; HIV=Human immunodeficiency virus; IDE=Infectious disease experts; IL=Interleukin; IRB=institutional review board; IVIG=Intravenous immunoglobulin; KNN=K-nearest neighbors; LP=*Legionella pneumophila*; LR+=Positive likelihood ratio; LR−=Negative likelihood ratio; LRTI=Lower respiratory tract infections; mAb=Monoclonal antibodies; MDD=Minimum detectable dose; MDS=Myelodysplastic syndrome; MP=*Mycoplasma* pneumonia; MPD=Myeloproliferative disease; NPV=Negative predictive value; PCT=Procalcitonin; PED=Pediatric emergency department; PPV=Positive predictive value; QA=Quality assurance; RSV=Respiratory syncytial virus; RV=Rhinovirus; SIRS=systemic inflammatory syndrome; SP=*Streptococcus pneumonia*; STARD=Standards for Reporting of Diagnostic Accuracy; SVM=Support vector machine; TNF=Tumor necrosis factor; URTI=Upper respiratory tract infection; UTI=Urinary tract infection; WBC=White blood cell; WS=Wilcoxon rank-sum.

In the context of the present invention, the following statistical terms may be used:

"TP" is true positive, means positive test result that accurately reflects the tested-for activity. For example in the context of the present invention a TP, is for example but not limited to, truly classifying a bacterial infection as such.

"TN" is true negative, means negative test result that accurately reflects the tested-for activity. For example in the context of the present invention a TN, is for example but not limited to, truly classifying a viral infection as such.

"FN" is false negative, means a result that appears negative but fails to reveal a situation. For example in the context of the present invention a FN, is for example but not limited to, falsely classifying a bacterial infection as a viral infection.

"FP" is false positive, means test result that is erroneously classified in a positive category. For example in the context of the present invention a FP, is for example but not limited to, falsely classifying a viral infection as a bacterial infection.

"Sensitivity" is calculated by TP/(TP+FN) or the true positive fraction of disease subjects.

"Specificity" is calculated by TN/(TN+FP) or the true negative fraction of non-disease or normal subjects.

"Total accuracy" is calculated by (TN+TP)/(TN+FP+TP+FN).

"Positive predictive value" or "PPV" is calculated by TP/(TP+FP) or the true positive fraction of all positive test results. It is inherently impacted by the prevalence of the disease and pre-test probability of the population intended to be tested.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

"MCC" (Mathews Correlation coefficient) is calculated as follows: MCC=(TP*TN−FP*FN)/{(TP+FN)*(TP+FP)*(TN+FP)*(TN+FN)}^0.5
where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Mathews correlation coefficient (MCC), or as a likelihood, odds ratio, Receiver Operating Characteristic (ROC) curve, Area Under the Curve (AUC) among other measures.

"Analytical accuracy" refers to the reproducibility and predictability of the measurement process itself, and may be summarized in such measurements as coefficients of variation (CV), Pearson correlation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC and MCC, time to result, shelf life, etc. as relevant.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

The term "determinant" as used herein refers to a disease associated parameter or biomarker.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Examples

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Methods

Study Population:

1002 patients with suspected acute infectious disease and non-infectious controls were prospectively recruited from Hillel-Yaffe and Bnai-Zion Medical Centers, Israel (NCT01917461). The study was conducted according to the guidelines and recommendations of Good Clinical Practice and the Declaration of Helsinki. Written informed consent was obtained from each participant or legal guardian, as applicable.

Pediatric patients (≤18 years) were recruited from pediatric emergency departments (PED), pediatric wards and surgical departments, and adults (>18 years) from emergency departments (ED), internal medicine departments and surgical departments. Informed consent was obtained from each participant or legal guardian, as applicable. Inclusion criteria for the infectious disease cohort included: clinical suspicion of an acute infectious disease, peak fever >37.5° C. since symptoms onset, and duration of symptoms ≤12 days. Inclusion criteria for the control group included: clinical impression of a non-infectious disease (e.g. trauma, stroke and myocardial infarction), or healthy subjects. Exclusion criteria included: evidence of any episode of acute infectious disease in the two weeks preceding enrollment; diagnosed congenital immune deficiency; current treatment with immunosuppressive or immunomodulatory therapy; active malignancy, proven or suspected human immunodeficiency virus (HIV)—1, hepatitis B virus (HBV), or hepatitis C virus (HCV) infection. Importantly, in order to enable broad generalization, antibiotic treatment at enrollment did not cause exclusion from the study.

Enrollment Process and Data Collection:

For each patient, the following baseline variables were recorded: demographics, physical examination, medical history (e.g. main complaints, underlying diseases, chronically-administered medications, comorbidities, time of symptom onset, and peak temperature), complete blood count (CBC) obtained at enrollment, and chemistry panel (e.g. creatinine, urea, electrolytes, and liver enzymes). A nasal swab was obtained from each patient for further microbiological investigation, and a blood sample was obtained for protein screening and validation. Additional samples were obtained as deemed appropriate by the physician (e.g. urine and stool samples in cases of suspected urinary tract infection [UTI], and gastroenteritis [GI] respectively). Radiological tests were obtained at the discretion of the physician (e.g. chest X-ray for suspected lower respiratory tract infection [LRTI]). Thirty days after enrollment, disease course and response to treatment were recorded. All information was recorded in a custom electronic case report form (eCRF).

Microbiological Investigation:

Patients underwent two multiplex-PCR diagnostic assays from nasal swab samples: (i) Seeplex® RV15 (n=713), for detection of parainfluenza virus 1, 2, 3, and 4, coronavirus 229E/NL63, adenovirus A/B/C/D/E, bocavirus 1/2/3/4, influenza virus A and B, metapneumovirus, coronavirus OC43, rhinovirus A/B/C, respiratory syncytial virus A and B, and Enterovirus, and (ii) Seeplex® PB6 (n=633) for detection of *Streptococcus pneumoniae, Haemophilus influenzae, Chlamydophila pneumoniae, Legionella pneumophila, Bordetella pertussis*, and *Mycoplasma pneumoniae*. Multiplex-PCR assays were performed by a certified service laboratory. Patients were also tested for additional pathogens according to their suspected clinical syndrome, including: blood culture (n=420), urine culture (n=188) and stool culture for *Shigella* spp., *Campylobacter* spp. and *Salmonella* spp. (n=66); serological testing (IgM and/or IgG) for cytomegalovirus (CMV), Epstein-Barr virus (EBV), *Mycoplasma* Pneumonia, and *Coxiella burnetii* (Q-Fever) (n=167, n=130, n=206 and n=41 respectively).

Figure 1:
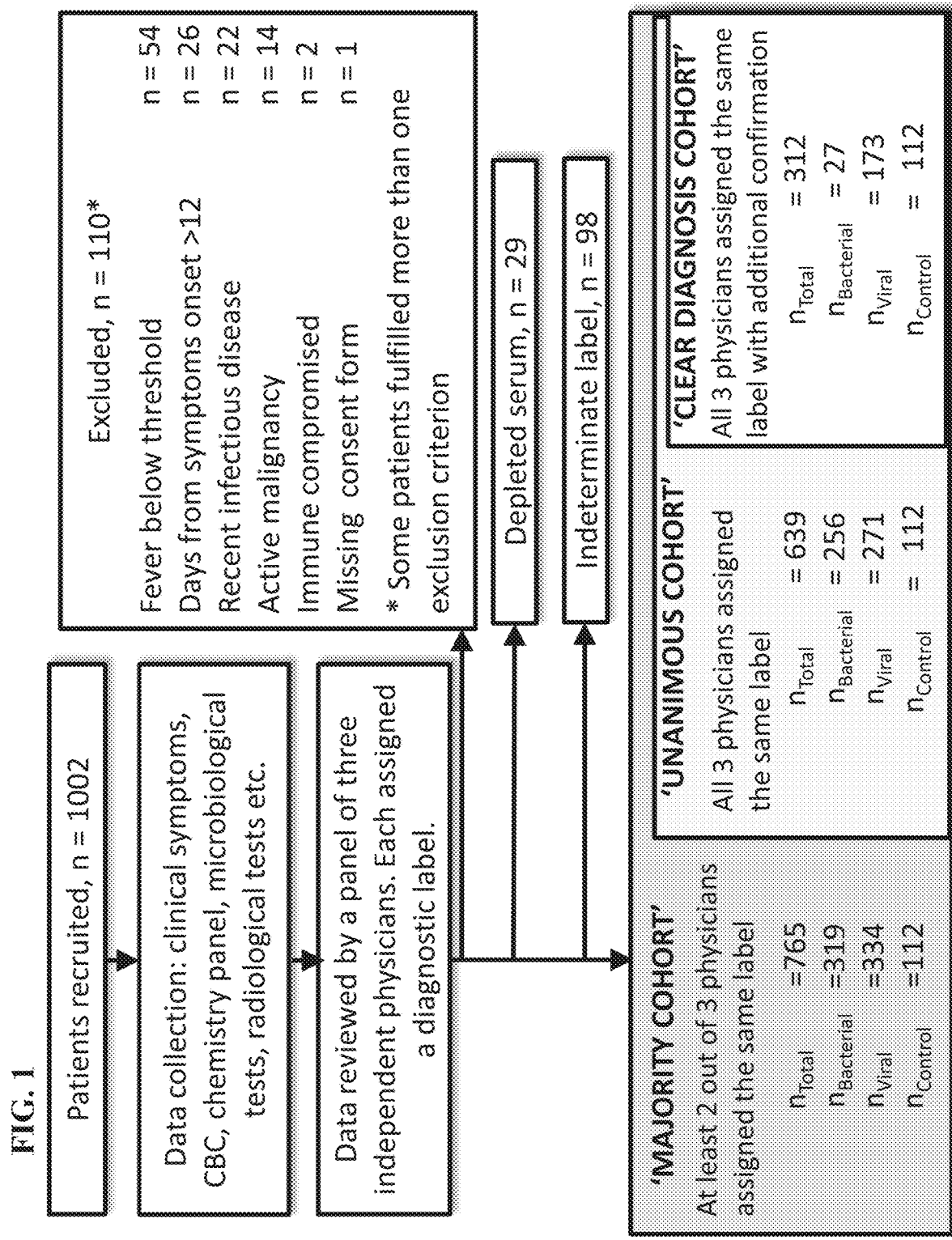
FIG. 1: Clinical study workflow.
Figure 2:
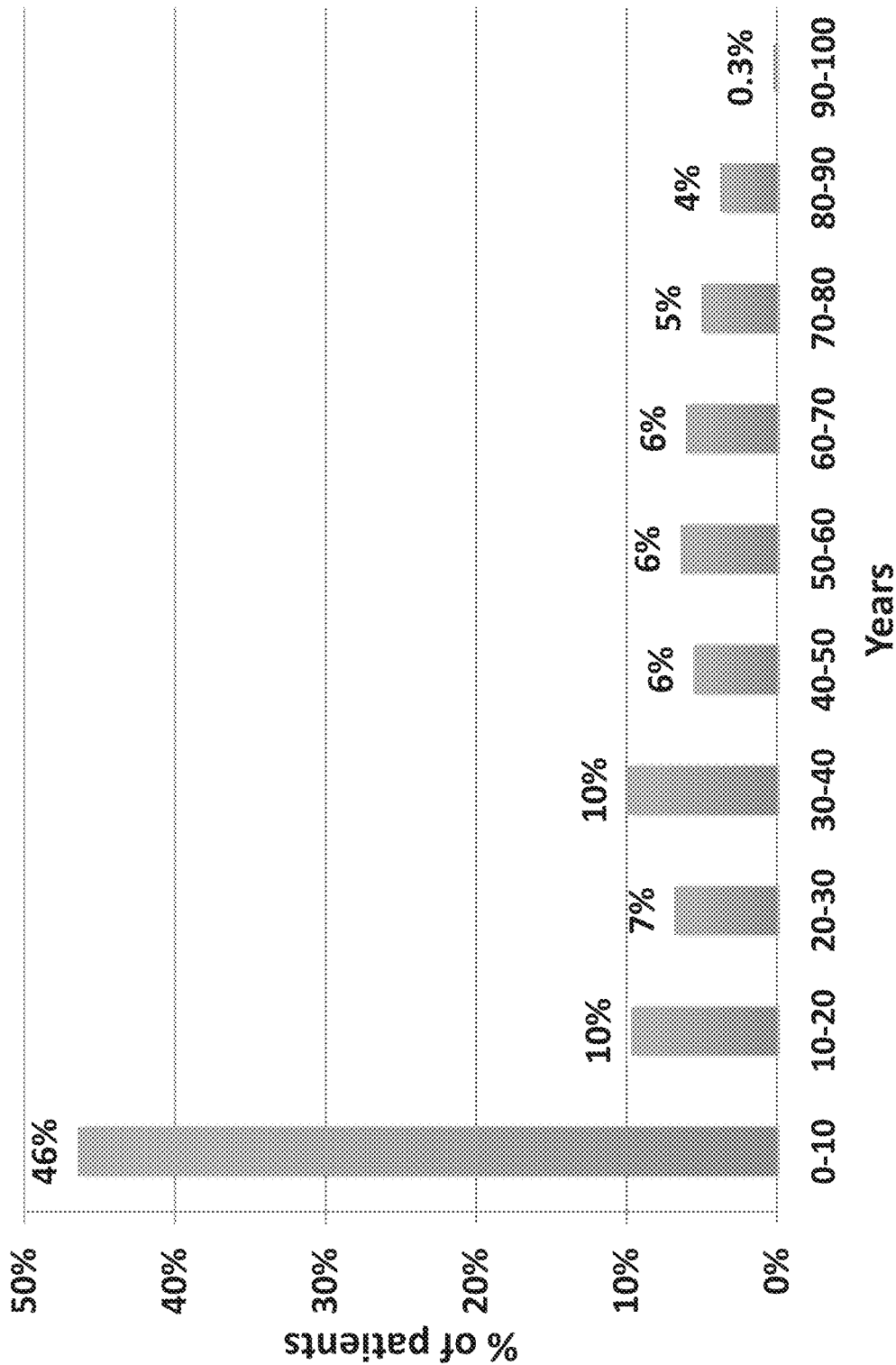
FIG. 2: Distribution of age of the patients enrolled in the clinical study.
Figure 3:
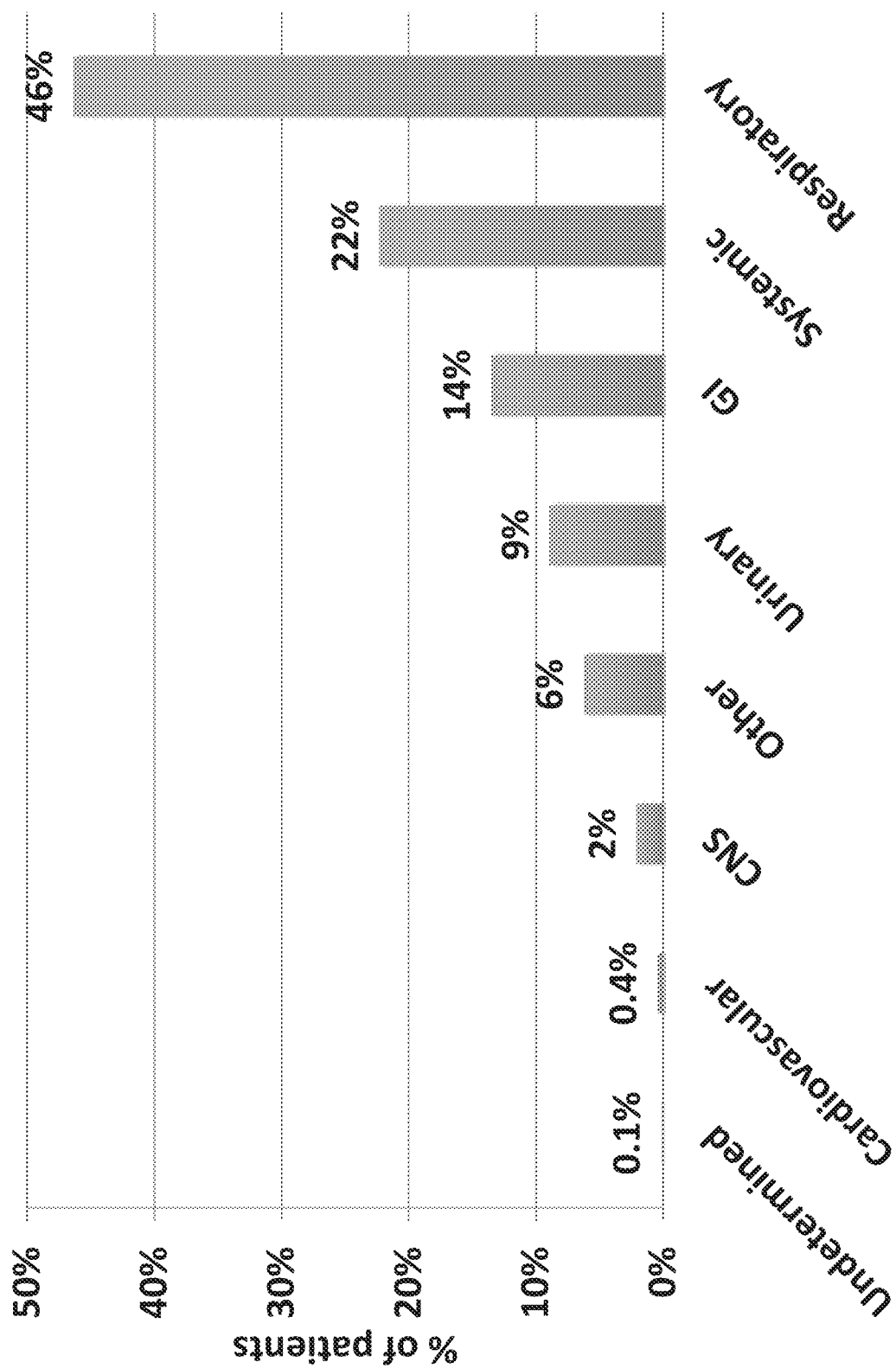
FIG. 3: Distribution of physiological systems of the infectious disease patients enrolled in the clinical study.
Figure 4:
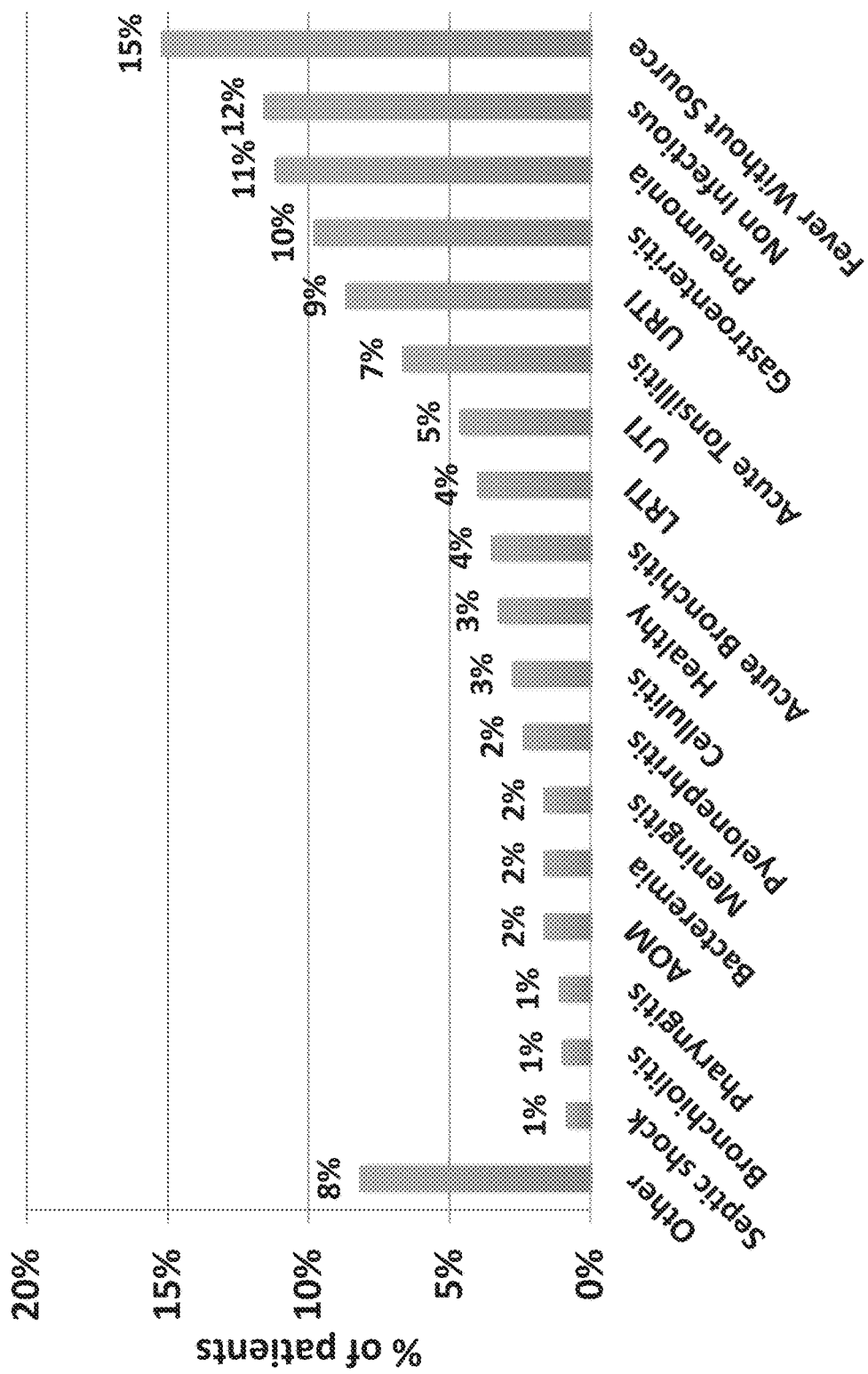
FIG. 4: Distribution of clinical syndromes of the infectious disease patients enrolled in the clinical study.
Figure 5:
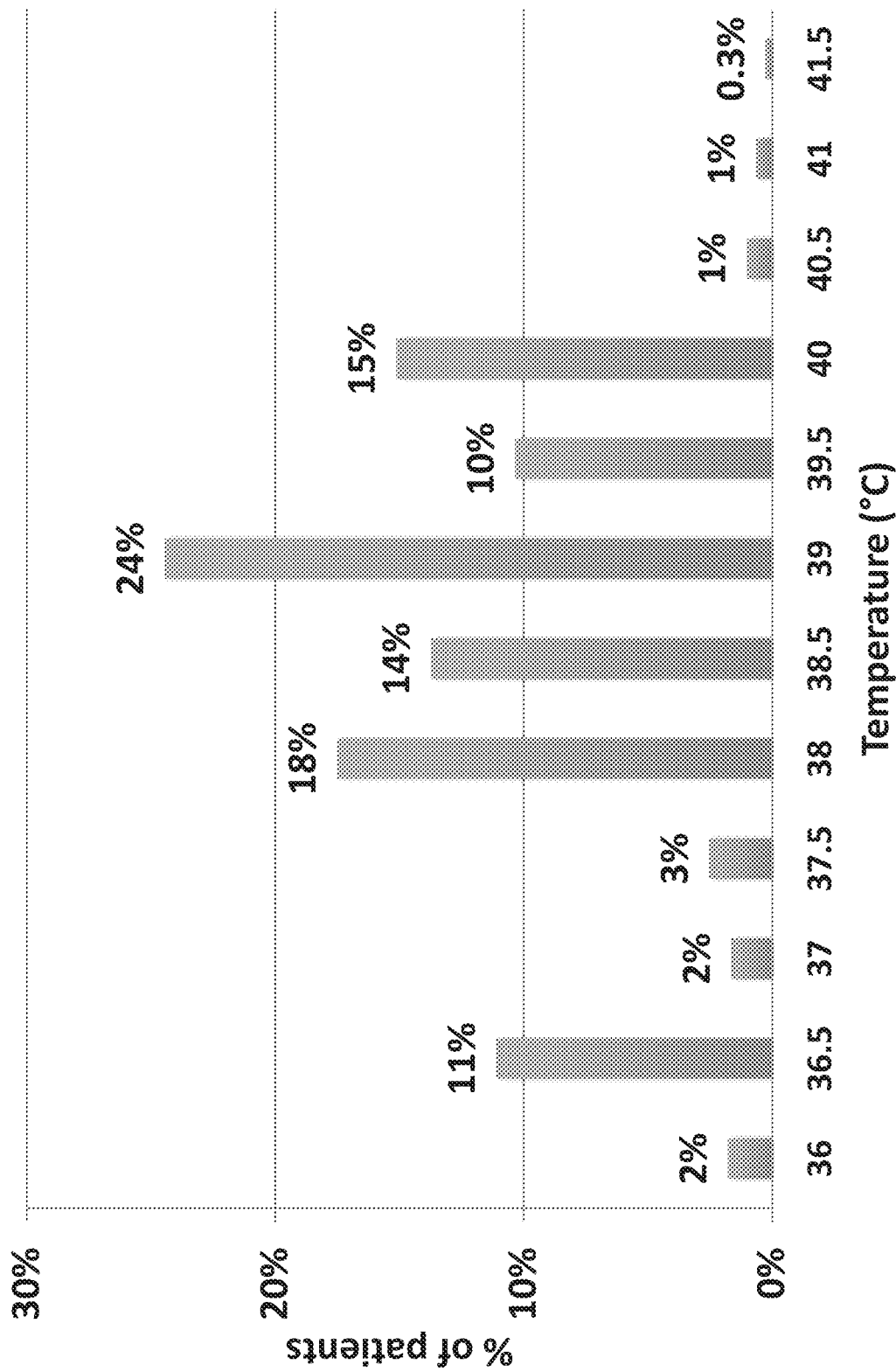
FIG. 5: Distribution of maximal body temperatures of the infectious disease patients enrolled in the clinical study.
Figure 6:
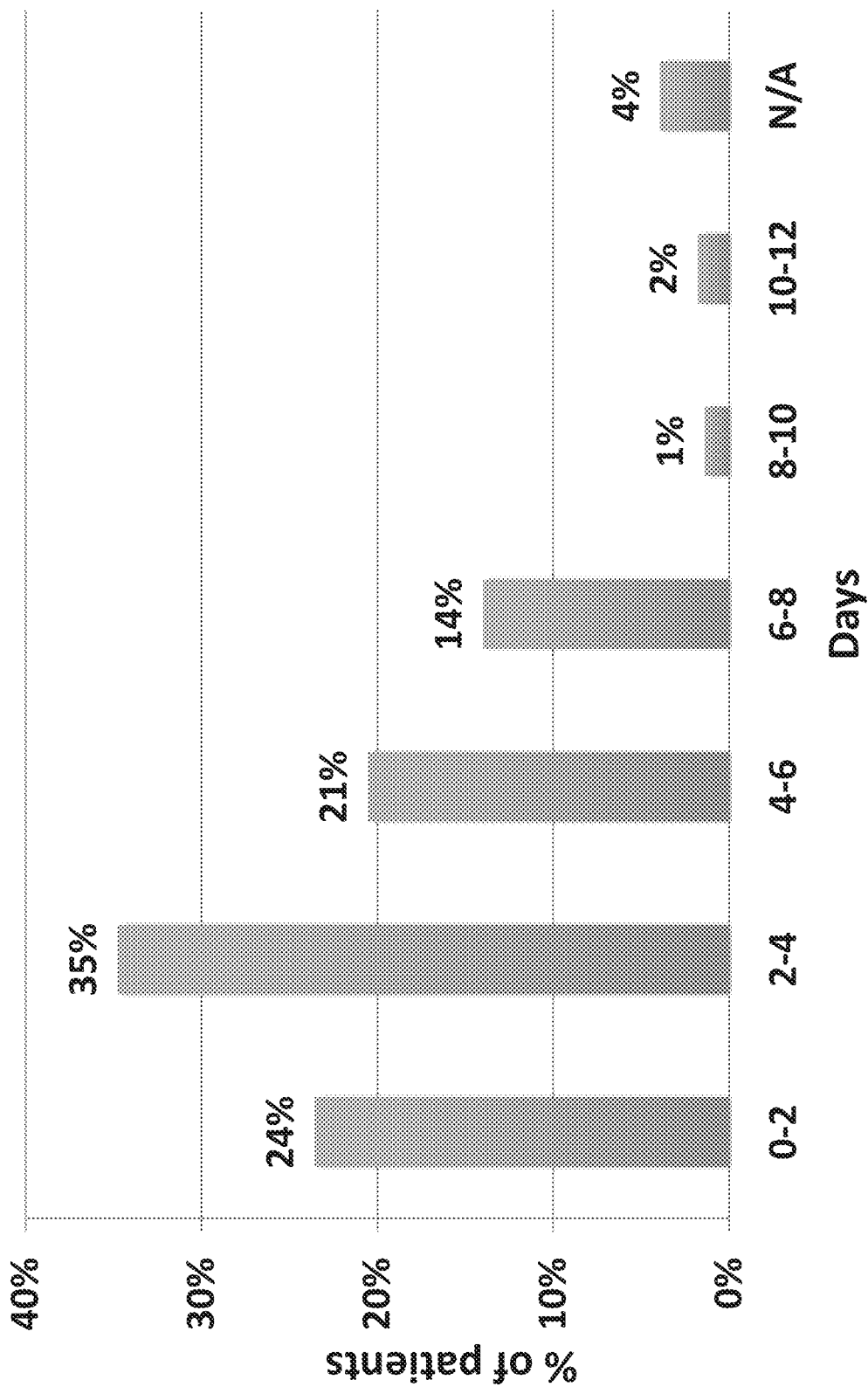
FIG. 6: Distribution of time from initiation of symptoms of the infectious disease patients enrolled in the clinical study.
Figure 7:
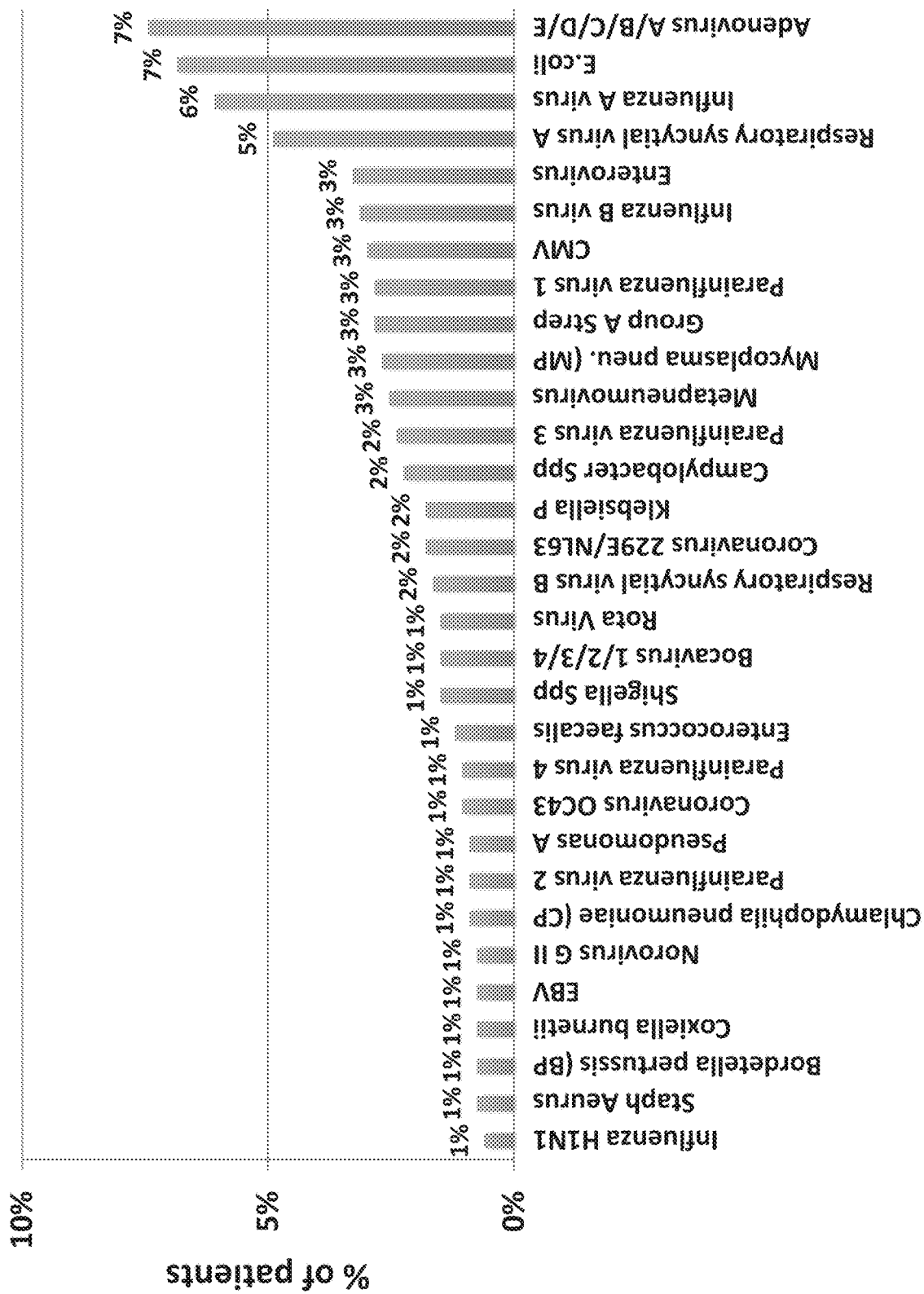
FIG. 7: Selected pathogens isolated from infectious disease patients enrolled in the clinical study.

Establishing the Reference Standard:

A rigorous composite reference standard was created following recommendations of the Standards for Reporting of Diagnostic Accuracy (STARD; FIG. 1).[1] First, a thorough clinical and microbiological investigation was performed for each patient as described above. Then, all the data collected throughout the disease course was reviewed by a panel of three physicians. For adult patients (>18 years) the panel included the attending physician and two infectious disease specialists, while for children and adolescents (≤18 years) it included the attending pediatrician, an infectious disease expert and a senior attending pediatrician. Each panel member assigned one of the following diagnostic labels to each patient: (i) bacterial; (ii) viral; (iii) no apparent infectious disease or healthy (controls); and (iv) mixed infections (bacteria plus virus). Importantly, the panel members were blinded to the labeling of their peers and to the results of the signature.

Patient Prognostic Measures:

Various clinical measures were used to retrospectively assess patient's prognosis such as ICU admission, need for mechanical ventilation or surgical interventions, hospital length of stay, patient re-admission to the hospital, and the manifestation of a severe clinical syndrome like bacteremia or septic shock.

Samples, Procedures and Protein Measurements:

Venous blood samples were stored at 4° C. for up to 5 hours on site and subsequently fractionated into plasma, serum and total leukocytes and stored at −80° C. Nasal swabs and stool samples were stored at 4° C. for up to 72 hours and subsequently transported to a certified service laboratory for multiplex PCR-based assay. TRAIL was measured using commercial ELISA kits (MeMed Diagnostics).

Statistical Analysis:

The primary analysis was based on area under the receiver operating characteristics curve (AUC), Sensitivity (TP/P), Specificity (TN/N), Positive predictive value (PPV=TP/[TP+FP]), Negative predictive value (NPV=TN/[TN+FN]), where P, N, TP and TN correspond to positives (bacterial patients), negatives (viral patients), true positives (correctly diagnosed bacterial patients), and true negatives (correctly diagnosed viral patients), respectively. Statistical analysis was performed with MATLAB.

Results

Patient Characteristics:

Three physicians independently assigned a label to each patient (either bacterial, viral, controls, or indeterminate). 98 patients were labeled as indeterminate, because the physicians could not establish disease etiology or there was no majority labeling. A detailed characterization of the analyzed cohort is depicted in FIGS. 2-7. Briefly, the cohort was balanced with respect to gender (47% females, 53% males) and included 56% pediatric patients (≤18 years) and 44% adults (>18 years). Patients presented with a wide range of clinical syndromes (e.g. RTI, UTI, and systemic infections), maximal temperatures (36-41.5° C.), and time from symptoms onset (0-12 days). Altogether, 56 pathogen species were detected that are responsible for the vast majority of acute infectious diseases in the Western world.

TRAIL as a Prognostic Marker

Figure 11:
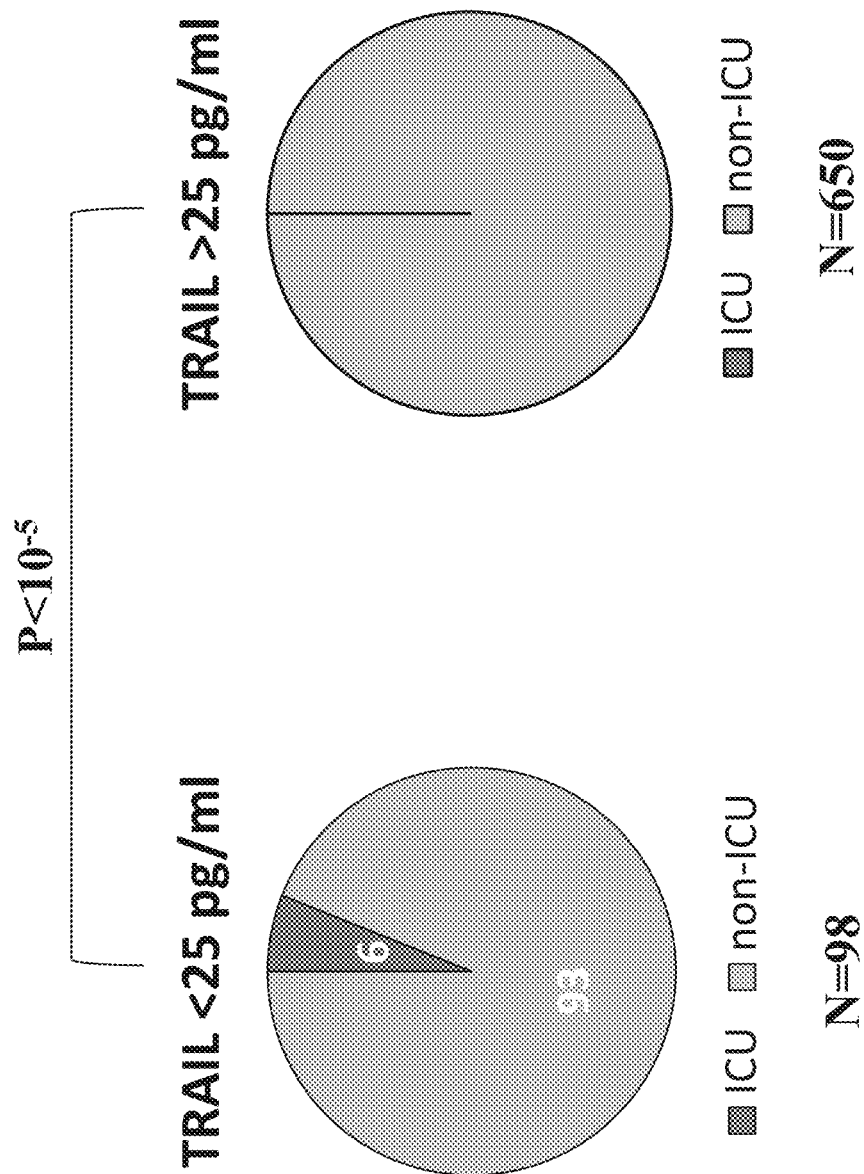
FIG. 11: Intensive care unit (ICU) admission rates in infectious patients with different TRAIL levels.
Figure 12:
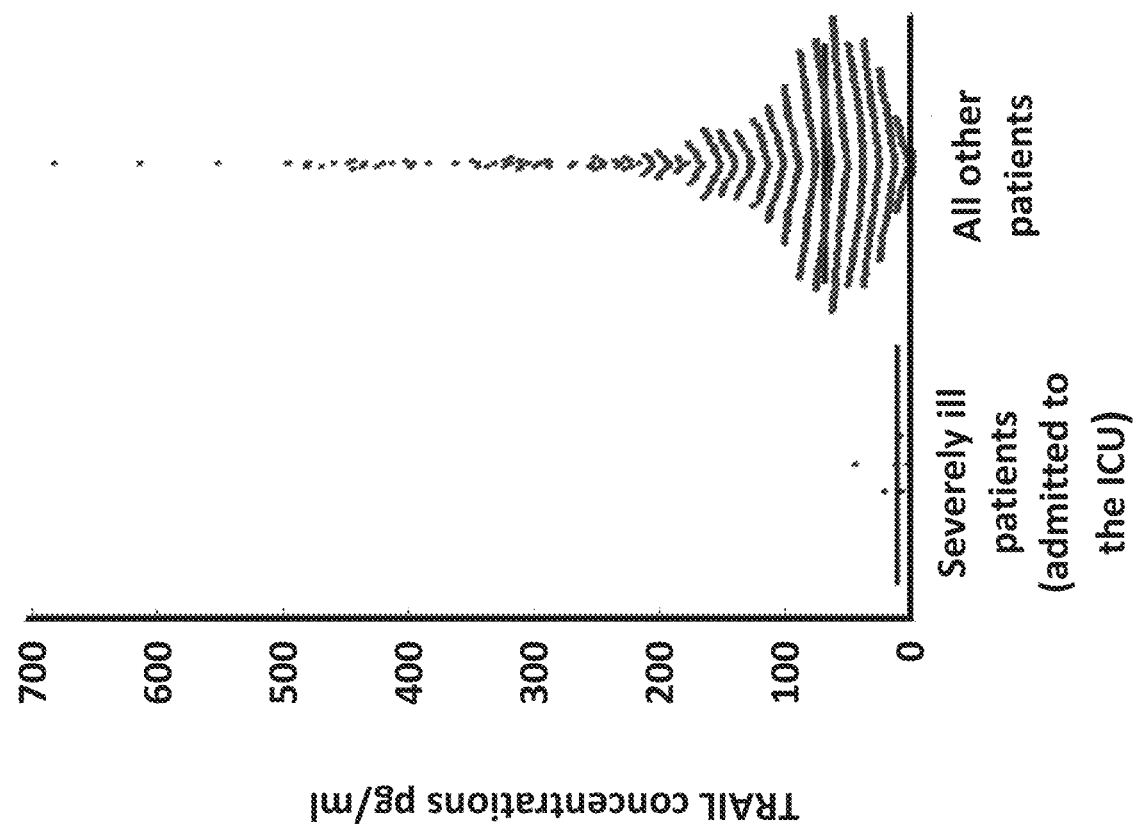
FIG. 12: Serum TRAIL levels are lower in patients admitted to the ICU.
Figure 13:
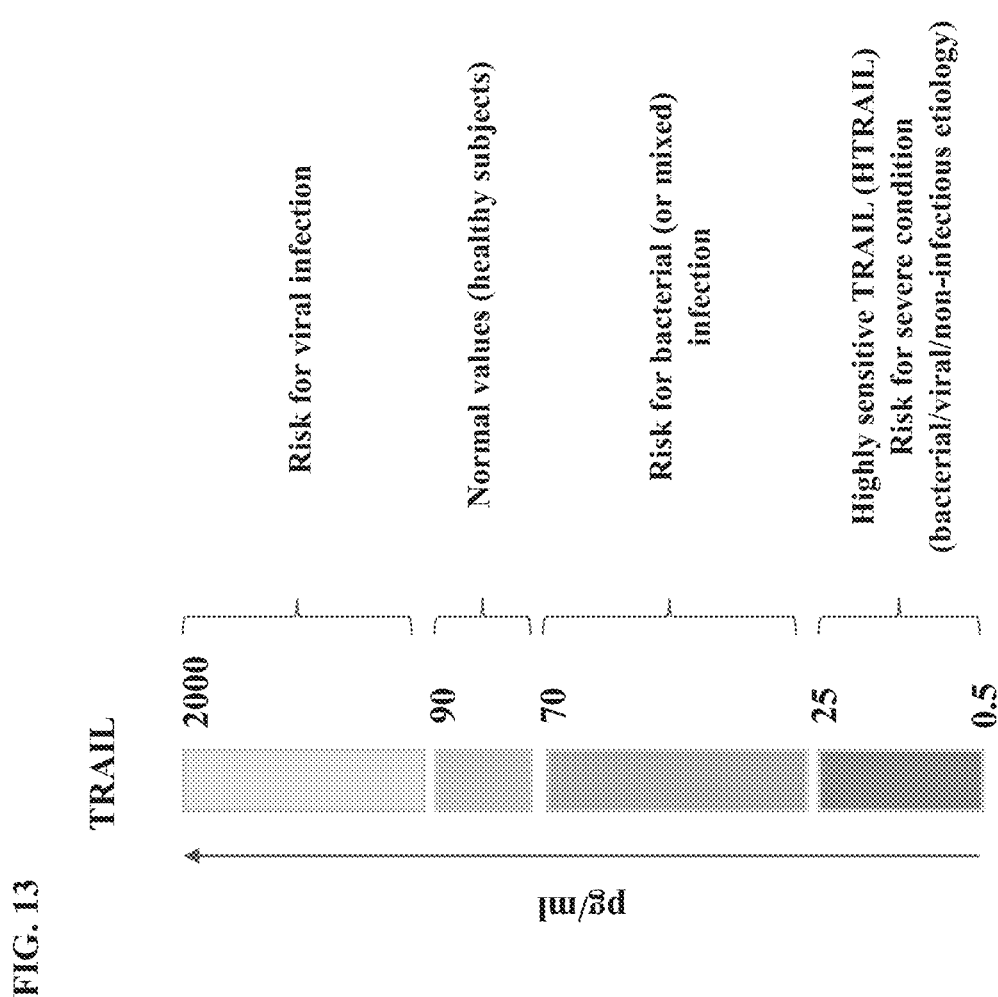
FIG. 13: TRAIL cutoffs indicative of different clinical states. Highly sensitive TRAIL (HTRAIL; 0.5-25 pg/ml) serves as an indicator for disease severity, while higher levels of TRAIL serves as indicators for bacterial infection (25-70 pg/ml), healthy state (70-90 pg/ml), or viral infections (90-3000 pg/ml).

In the studied cohort, 667 patients had TRAIL levels higher than 25 pg/ml and 98 patients had TRAIL levels lower than 25 pg/ml (FIG. 8), out of which 89 had a bacterial etiology, 4 viral etiology and 5 with non-infectious condition. The 98 patients with TRAIL levels lower than 25 pg/ml had poorer patient prognosis and outcome, and higher disease severity compared to patients with higher TRAIL levels. For example, their hospitalization duration was close to 4-fold longer compared to patients with higher TRAIL levels (7.5±1.17 vs 1.9±0.1, days, average±standard error, $P<10^{-5}$; FIG. 11). All patients from the infectious disease group that required mechanical ventilation and ICU admission had TRAIL levels lower than 25 pg/ml (6/93 TRAIL<25 pg/ml vs 0/560 TRAIL>25 pg/ml, $P<10^{-5}$; FIG.

12). Median serum concentrations were 9 pg/ml vs. 80 pg respectively, (ranksum P<0.001, FIG. 12), for severely ill and all other patients respectively. Strikingly, the lowest TRAIL levels (<5 pg/ml) were measured in the only two children that died in the entire cohort.

REFERENCES

1. Bossuyt, P. M. et al. The STARD Statement for Reporting Studies of Diagnostic Accuracy: Explanation and Elaboration. Ann Intern Med 138, W1-W12 (2003).
2. Niemz, A., Ferguson, T. M. & Boyle, D. S. Point-of-care nucleic acid testing for infectious diseases. Trends Biotechnol. 29, 240-250 (2011).
3. Craw, P. & Balachandran, W. Isothermal nucleic acid amplification technologies for point-of-care diagnostics: a critical review. Lab Chip 12, 2469-2486 (2012).
4. Kim, K. H., Shin, J. H. & Kim, S. Y. The Clinical Significance of Nasopharyngeal Carriages in Immunocompromised Children as Assessed. The Korean Journal of Hematology 44, 220 (2009).
5. Shin, J. H., Han, H. Y. & Kim, S. Y. Detection of nasopharyngeal carriages in children by multiplex reverse transcriptase-polymerase chain reaction. Korean Journal of Pediatrics 52, 1358 (2009).
6. Jung, C. L., Lee, M. A. & Chung, W. S. Clinical Evaluation of the Multiplex PCR Assay for the Detection of Bacterial Pathogens in Respiratory Specimens from Patients with Pneumonia. Korean Journal of Clinical Microbiology 13, 40 (2010).
7. Rhedin, S. et al. Clinical Utility of PCR for Common Viruses in Acute Respiratory Illness. Pediatrics peds. 2013-3042 (2014). doi:10.1542/peds.2013-3042.
8. Bogaert, D., De Groot, R. & Hermans, P. W. M. *Streptococcus pneumoniae* colonisation: the key to pneumococcal disease. Lancet Infect Dis 4, 144-154 (2004).
9. Spuesens, E. B. M. et al. Carriage of *Mycoplasma pneumoniae* in the Upper Respiratory Tract of Symptomatic and Asymptomatic Children: An Observational Study. PLoS Med 10, e1001444 (2013).

---

What is claimed is:

1. A method for triaging subjects comprising measuring the TRAIL protein level in a blood sample of a subject showing symptoms of an infectious disease, wherein the subject has a normal troponin level, and wherein when the TRAIL level is below 30 pg/ml, the subject is admitted to a hospital.

2. The method of claim 1 further comprising managing the subject with a management selected from the group consisting of mechanical ventilation, invasive monitoring, last-resort drug, sedation, intensive care admission and surgical intervention.

3. The method of claim 1, wherein said blood sample is a fraction of whole blood.

4. The method of claim 3, wherein said fraction is serum or plasma.

5. The method of claim 1, wherein said blood sample comprises cells selected from the group consisting of lymphocytes, monocytes and granulocytes.

6. The method of claim 1, wherein said measuring is determined electrophoretically or immunochemically.

7. The method of claim 6, wherein said immunochemical determination is measured by lateral flow immunoassay, flow cytometry, radioimmunoassay, immunofluorescence or by an enzyme-linked immunosorbent assay.

8. The method of claim 1, wherein the subject has an infectious disease.

9. The method of claim 1, wherein the symptoms comprise fever.

10. The method of claim 1, wherein the triaging further comprises measuring the level of at least one additional determinant selected from the group consisting of IP10, CRP, PCT, and IL-6.

11. The method of claim 1, wherein when the TRAIL level is below 25 pg/ml, the subject is admitted to a hospital.

* * * * *